US012617798B2

(12) United States Patent
Lerner et al.

(10) Patent No.: US 12,617,798 B2
(45) Date of Patent: May 5, 2026

(54) IMIDAZOPYRAZNE DERIVATIVES

(71) Applicant: Hoffmann-La Roche Inc., Little Falls, NJ (US)

(72) Inventors: Christian Lerner, Bottmingen (CH); Yongqiang Liu, Shanghai (CN); Song Yang, Shanghai (CN); Chengang Zhou, Shanghai (CN)

(73) Assignee: Hoffmann-La Roche Inc., Little Falls, NJ (US)

( * ) Notice: Subject to any disclaimer, the term of this patent is extended or adjusted under 35 U.S.C. 154(b) by 663 days.

(21) Appl. No.: 18/070,648

(22) Filed: Nov. 29, 2022

(65) Prior Publication Data

US 2023/0203047 A1 Jun. 29, 2023

Related U.S. Application Data

(63) Continuation of application No. PCT/EP2021/064473, filed on May 31, 2021.

(30) Foreign Application Priority Data

Jun. 1, 2020 (WO) ................ PCT/CN2020/093723

(51) Int. Cl.
*C07D 487/04* (2006.01)

(52) U.S. Cl.
CPC .................................. *C07D 487/04* (2013.01)

(58) Field of Classification Search
CPC ............................... C07D 487/04; A61P 31/04
See application file for complete search history.

(56) References Cited

U.S. PATENT DOCUMENTS

2014/0155385 A1 * 6/2014 Barf et al.

FOREIGN PATENT DOCUMENTS

| | | |
|---|---|---|
| WO | 2009/024585 A2 | 2/2009 |
| WO | 2010/027500 A1 | 3/2010 |
| WO | 2012/168733 A1 | 12/2012 |
| WO | 2020/126953 | 6/2020 |
| WO | 2020/126953 A1 | 6/2020 |

OTHER PUBLICATIONS

International Preliminary Report on Patentability—PCT/EP2021/064473 issued Dec. 6, 2022, pp. 1-8.
International Search Report—PCT/EP2021/064473 (with Written Opinion) mailed Aug. 30, 2021, pp. 1-10.

* cited by examiner

*Primary Examiner* — Kortney L. Klinkel
*Assistant Examiner* — Jackson J Hernandez
(74) *Attorney, Agent, or Firm* — Genentech, Inc.

(57) ABSTRACT

The invention provides novel imidazopyrazine derivatives having the general formula (I), and pharmaceutically acceptable salts thereof, wherein $X^1$ to $X^4$, $R^1$ to $R^5$, $R^8$ to $R^{10}$, A, and $L^1$ are as described herein:

(I)

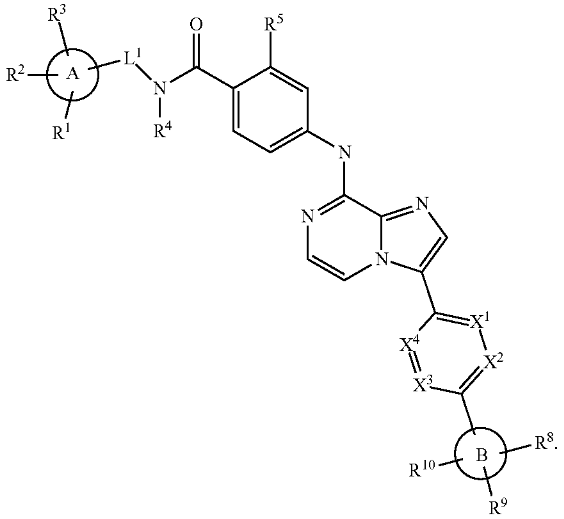

Further provided are pharmaceutical compositions including the compounds, processes of manufacturing the compounds and methods of using the compounds as medicaments, in particular methods of using the compounds as antibiotics for the treatment or prevention of bacterial infections and resulting diseases.

20 Claims, No Drawings

IMIDAZOPYRAZNE DERIVATIVES

CROSS-REFERENCE TO RELATED APPLICATIONS

This application is a Continuation Application of International Patent Application No. PCT/EP2021/064473, filed on May 31, 2021, which claims benefit of priority to International Patent Application No. PCT/CN2020/093723, filed on Jun. 1, 2020, each of which is incorporated herein by reference in its entirety.

BACKGROUND

The present invention relates to novel imidazopyrazine derivatives which exhibit antibacterial properties. The invention also relates to methods of using the compounds for the treatment or prevention of bacterial infections and resulting diseases, in particular for the treatment or prevention of infections with *Acinetobacter baumannii* and/or *Pseudomonas aeruginosa* and resulting diseases.

*Acinetobacter baumannii* and *Pseudomonas aeruginosa* are Gram-negative, aerobic, nonfermenting bacteria recognized over the last decades as emergining pathogens with very limited treatment options.

Carbapenem-resistant *A. baumannii* and Multi-Drug Resistant (MDR) *P. aeruginosa* are considered to be urgent and serious threats, respectively, by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents. *A. baumannii* and *P. aeruginosa* are often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinants and shows an environmental persistance that allows its survival and spread in the nosocomial setting, making this organism a frequent cause of outbreaks of infection and an endemic, health care-associated pathogen. *P. aeruginosa* infections also usually occur in the nosocomial setting or in patients with a weakened immune system. It is particularly dangerous for patients with chronic lung diseases. *P. aeruginosa* has intrinsic resistance to many different types of chemotherapeutic agents and antibiotics, making it a very difficult pathogen to eliminate.

Due to increasing antibiotic resistance to most if not all available therapeutic options, MDR *A. baumannii* infections, especially those caused by Carbapenem resistant *A. baumannii*, are extremely difficult or even impossible to treat with high mortality rate as well as increased morbidity and length of stay in intensive care unit. Similarly, some types of MDR *P. aeruginosa* are resistant to nearly all antibiotics, including carbapenems. The threat remains high. The 2019 report by the CDC reported 32,600 cases and 2,700 deaths in US hospitals. *Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*. The present invention provides novel compounds which exhibit activity against drug-susceptible as well as drug-resistant strains of *Acinetobacter baumannii* and/or *Pseudomonas aeruginosa*.

SUMMARY OF THE DISCLOSURE

In a first aspect, the present invention provides compounds of formula (I)

(I)

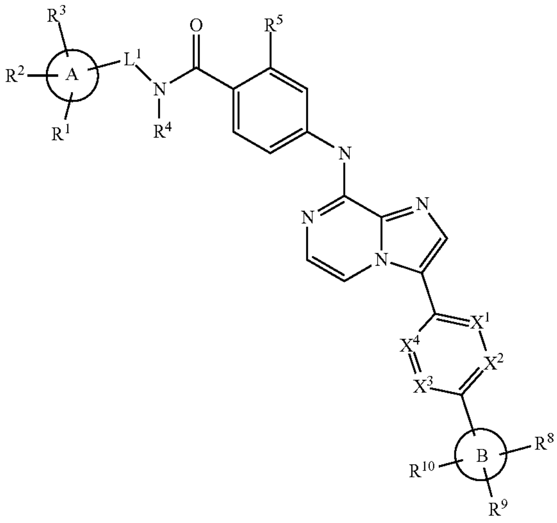

or a pharmaceutically acceptable salts thereof, wherein $X^1$ to $X^4$, $R^1$ to $R^5$, $R^8$ to $R^{10}$, A, and $L^1$ are as described herein.

In one aspect, the present invention provides a process of manufacturing the compounds of formula (I) described herein, or pharmaceutically acceptable salts thereof, comprising:

(i) Suzuki coupling of a heteroaryl halide C1, wherein $R^1$ to $R^5$, A, and $L^1$ are as defined herein and "Hal" is a halogen, preferably iodine, (C1)

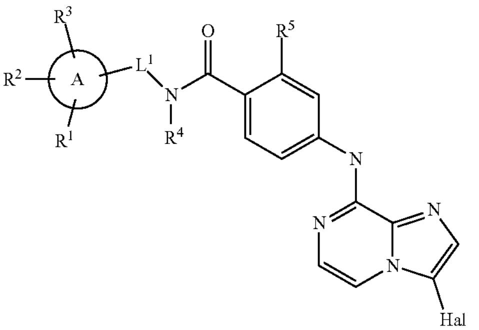

with a boronic acid (ester) B1, wherein $X^1$ to $X^4$, $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(B1)

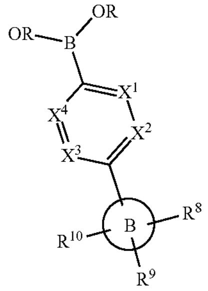

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I); or (ii) Suzuki coupling of an aryl/heteroaryl halide E1, wherein $R^1$ to $R^5$, A, $L^1$, and $X^1$ to $X^4$ are as defined herein and "Hal" is a halogen, preferably chlorine, (E1)

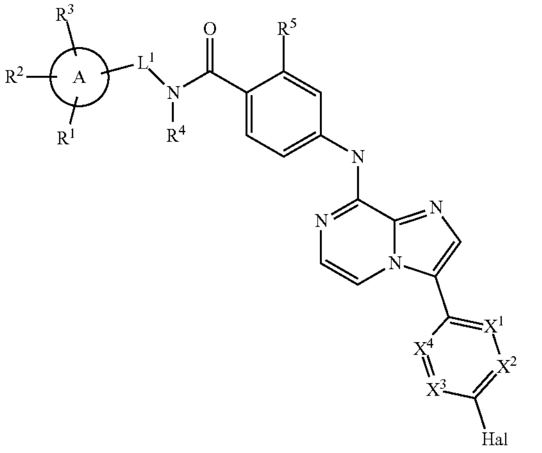

with a boronic acid (ester) I1, wherein $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(I1)

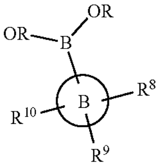

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I); to afford said compound of formula (I).

In a further aspect, the present invention provides a compound of formula (I) as described herein, when manufactured according to the processes described herein.

In a further aspect, the present invention provides a compound of formula (I) as described herein, or a pharmaceutically acceptable salt thereof, for use as therapeutically active substance.

In a further aspect, the present invention provides a pharmaceutical composition comprising a compound of formula (I) as described herein, or a pharmaceutically acceptable salt thereof, and a therapeutically inert carrier.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a further aspect, the present invention provides a compound of formula (I) as described herein, or a pharmaceutically acceptable salt thereof, for use in the treatment or prevention of infections and resulting diseases caused by Gram-negative bacteria.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

DETAILED DESCRIPTION OF THE DISCLOSURE

Definitions

Features, integers, characteristics, compounds, chemical moieties or groups described in conjunction with a particular aspect, embodiment or example of the invention are to be understood to be applicable to any other aspect, embodiment or example described herein, unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The following definitions are provided to facilitate understanding of certain terms used frequently herein and are not meant to limit the scope of the present disclosure. All references referred to herein are incorporated by reference in their entirety.

The term "alkyl" refers to a mono- or multivalent, e.g., a mono- or bivalent, linear or branched saturated hydrocarbon group of 1 to 6 carbon atoms ("$C_1$-$C_6$-alkyl"), e.g., 1, 2, 3, 4, 5, or 6 carbon atoms. In some embodiments, the alkyl group contains 1 to 3 carbon atoms, e.g., 1, 2 or 3 carbon atoms. Some non-limiting examples of alkyl include methyl, ethyl, propyl, 2-propyl (isopropyl), n-butyl, iso-butyl, secbutyl, tert-butyl, and 2,2-dimethylpropyl. A particularly preferred, yet non-limiting example of alkyl is methyl.

The term "alkoxy" refers to an alkyl group, as previously defined, attached to the parent molecular moiety via an oxygen atom. Unless otherwise specified, the alkoxy group contains 1 to 6 carbon atoms ("$C_1$-$C_6$-alkoxy"). In some preferred embodiments, the alkoxy group contains contains 1 to 4 carbon atoms. In still other embodiments, the alkoxy group contains 1 to 3 carbon atoms. Some non-limiting examples of alkoxy groups include methoxy, ethoxy, n-propoxy, isopropoxy, n-butoxy, isobutoxy and tert-butoxy. A particularly preferred, yet non-limiting example of alkoxy is methoxy.

The term "halogen" or "halo" refers to fluoro (F), chloro (Cl), bromo (Br), or iodo (I). Preferably, the term "halogen" or "halo" refers to fluoro (F), chloro (Cl) or bromo (Br). Particularly preferred, yet non-limiting examples of "halogen" or "halo" are fluoro (F) and chloro (Cl).

The term "aminoalkyl" refers to an alkyl group, wherein at least one of the hydrogen atoms of the alkyl group has been replaced by an amino group. Preferably, "aminoalkyl" refers to an alkyl group wherein 1, 2 or 3 hydrogen atoms of the alkyl group have been replaced by an amino group. Preferred, yet non-limiting examples of aminoalkyl are aminomethyl and 1-aminoethyl.

The term "carbamoylalkyl" refers to an alkyl group, wherein at least one of the hydrogen atoms of the alkyl group has been replaced by a carbamoyl group. Preferably, "carbamoylalkyl" refers to an alkyl group wherein 1, 2 or 3 hydrogen atoms of the alkyl group have been replaced by a carbamoyl group. Preferred, yet non-limiting examples of carbamoylalkyl are carbamoylmethyl, 1-carbamoylethyl, and 2-carbamoylethyl.

The term "carboxyalkyl" refers to an alkyl group, wherein at least one of the hydrogen atoms of the alkyl group has been replaced by a carboxy group. Preferably, "carboxyalkyl" refers to an alkyl group wherein 1, 2 or 3 hydrogen atoms of the alkyl group have been replaced by a carboxy group. Preferred, yet non-limiting examples of carboxyalkyl are carboxymethyl, 1-carboxyethyl, and 2-carboxyethyl.

The term "heterocyclyl" refers to a saturated or partly unsaturated mono- or bicyclic, preferably monocyclic ring system of 3 to 14 ring atoms, preferably 3 to 10 ring atoms, more preferably 3 to 6 ring atoms, wherein 1, 2, or 3 of said ring atoms are heteroatoms selected from N, O and S, the remaining ring atoms being carbon. Preferably, 1 to 2 of said ring atoms are selected from N and O, the remaining ring atoms being carbon. More preferably, 1 of said ring atoms is N, the remaining ring atoms being carbon. "Bicyclic heterocyclyl" refers to heterocyclic moieties consisting of two cycles having two ring atoms in common, i.e., the bridge separating the two rings is either a single bond or a chain of one or two ring atoms, and to spirocyclic moieties, i.e., the two rings are connected via one common ring atom. Some non-limiting examples of heterocyclyl groups include azetidin-3-yl, azetidin-2-yl, oxetan-3-yl, oxetan-2-yl, 2-oxopyrrolidin-1-yl, 2-oxopyrrolidin-3-yl, 5-oxopyrrolidin-2-yl, 5-oxopyrrolidin-3-yl, 2-oxo-1-piperidyl, 2-oxo-3-piperidyl, 2-oxo-4-piperidyl, 6-oxo-2-piperidyl, 6-oxo-3-piperidyl, 1-piperidinyl, 2-piperidinyl, 3-piperidinyl, 4-piperidinyl, morpholino, morpholin-2-yl, morpholin-3-yl, pyrrolidinyl (e.g., pyrrolidin-3-yl), piperazinyl (e.g., piperazin-1-yl), 3-azabicyclo[3.1.0]hexan-6-yl, or 2,5-diazabicyclo[2.2.1]heptan-2-yl. Particularly preferred, yet non-limiting examples of heterocyclyl include piperidyl and azetidinyl.

The term "heteroaryl" refers to a mono- or multivalent, monocyclic or bicyclic, preferably bicyclic ring system having a total of 5 to 14 ring members, preferably, 5 to 12 ring members, and more preferably 5 to 10 ring members, wherein at least one ring in the system is aromatic, and at least one ring in the system contains one or more heteroatoms. Preferably, "heteroaryl" refers to a 5-10 membered heteroaryl comprising 1, 2, 3 or 4 heteroatoms independently selected from O, S and N. Most preferably, "heteroaryl" refers to a 5-10 membered heteroaryl comprising 1 to 2 heteroatoms independently selected from O and N. Some non-limiting examples of heteroaryl include 2-pyridyl, 3-pyridyl, 4-pyridyl, indol-1-yl, 1H-indol-2-yl, 1H-indol-3-yl, 1H-indol-4-yl, 1H-indol-5-yl, 1H-indol-6-yl, 1H-indol-7-yl, 1,2-benzoxazol-3-yl, 1,2-benzoxazol-4-yl, 1,2-benzoxazol-5-yl, 1,2-benzoxazol-6-yl, 1,2-benzoxazol-7-yl, 1H-indazol-3-yl, 1H-indazol-4-yl, 1H-indazol-5-yl, 1H-indazol-6-yl, 1H-indazol-7-yl, pyrazol-1-yl, 1H-pyrazol-3-yl, 1H-pyrazol-4-yl, 1H-pyrazol-5-yl, imidazol-1-yl, 1H-imidazol-2-yl, 1H-imidazol-4-yl, 1H-imidazol-5-yl, oxazol-2-yl, oxazol-4-yl, oxazol-5-yl, thiazol-4-yl, and 1,2,4-oxadiazol-3-yl. A preferred, yet non-limiting example of "heteroaryl" includes pyrazolyl, e.g. 1H-pyrazol-4-yl.

The term "hydroxy" refers to an —OH group.

The term "amino" refers to an —$NH_2$ group.

The term "cyano" refers to a —CN (nitrile) group.

The term "carbamoyl" refers to a —C(O)$NH_2$ group.

The term "carboxy" refers to a —C(O)OH group (carboxylic acid).

The term "haloalkyl" refers to an alkyl group, wherein at least one of the hydrogen atoms of the alkyl group has been replaced by a halogen atom, preferably fluoro. Preferably, "haloalkyl" refers to an alkyl group wherein 1, 2 or 3 hydrogen atoms of the alkyl group have been replaced by a halogen atom, most preferably fluoro. Particularly preferred, yet non-limiting examples of haloalkyl are trifluoromethyl, trifluoroethyl, 2-fluoroethyl, and 2,2-difluoroethyl.

The term "cyanoalkyl" refers to an alkyl group, wherein at least one of the hydrogen atoms of the alkyl group has been replaced by a cyano group. Preferably, "cyanoalkyl" refers to an alkyl group wherein 1, 2 or 3 hydrogen atoms of the alkyl group have been replaced by a cyano group. Particularly preferred, yet non-limiting examples of cyanoalkyl are cyanomethyl, 1-cyanoethyl, and 2-cyanoethyl.

The term "haloalkoxy" refers to an alkoxy group, wherein at least one of the hydrogen atoms of the alkoxy group has been replaced by a halogen atom, preferably fluoro. Preferably, "haloalkoxy" refers to an alkoxy group wherein 1, 2 or 3 hydrogen atoms of the alkoxy group have been replaced by a halogen atom, most preferably fluoro. Particularly preferred, yet non-limiting examples of haloalkoxy are difluoromethoxy and trifluoromethoxy.

The term "alkoxyalkyl" refers to an alkyl group, wherein at least one of the hydrogen atoms of the alkyl group has been replaced by an alkoxy group. Preferably, "alkoxyalkyl" refers to an alkyl group wherein 1, 2 or 3 hydrogen atoms of the alkyl group have been replaced by an alkoxy group. A particular, yet non-limiting example of an alkoxyalkyl group is 2-methoxyethyl.

The term "hydroxyalkyl" refers to an alkyl group, wherein at least one of the hydrogen atoms of the alkyl group has been replaced by a hydroxy group. Preferably, "hydroxyalkyl" refers to an alkyl group wherein 1, 2 or 3 hydrogen atoms, most preferably 1 hydrogen atom of the alkyl group have been replaced by a hydroxy group. Preferred, yet non-limiting examples of hydroxyalkyl are hydroxymethyl, hydroxyethyl (e.g. 2-hydroxyethyl), and 3-hydroxy-3-methyl-butyl.

The term "pharmaceutically acceptable salt" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, trifluoroacetic acid, propionic acid, glycolic acid, pyruvic acid, oxalic acid, maleic acid, malonic acid, succinic acid, fumaric acid, tartaric acid, lactic acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are hydrochlorides, fumarates, lactates (in particular derived from L-(+)-lactic acid), tartrates (in particular derived from L-(+)-tartaric acid) and trifluoroacetates.

The compounds of formula (I) can contain several asymmetric centers and can be present in the form of optically pure enantiomers, mixtures of enantiomers such as, for example, racemates, optically pure diastereioisomers, mixtures of diastereoisomers, diastereoisomeric racemates or mixtures of diastereoisomeric racemates.

According to the Cahn-Ingold-Prelog Convention, the asymmetric carbon atom can be of the "R" or "S" configuration.

The term "treatment" as used herein includes: (1) inhibiting the state, disorder or condition (e.g. arresting, reducing or delaying the development of the disease, or a relapse thereof in case of maintenance treatment, of at least one clinical or subclinical symptom thereof); and/or (2) relieving the condition (i.e., causing regression of the state, disorder or condition or at least one of its clinical or subclinical symptoms). The benefit to a patient to be treated is either statistically significant or at least perceptible to the patient or to the physician. However, it will be appreciated that when a medicament is administered to a patient to treat a disease, the outcome may not always be effective treatment.

The term "prophylaxis" as used herein includes: preventing or delaying the appearance of clinical symptoms of the state, disorder or condition developing in a mammal and especially a human that may be afflicted with or predisposed to the state, disorder or condition but does not yet experience or display clinical or subclinical symptoms of the state, disorder or condition.

The term "mammal" as used herein includes both humans and non-humans and includes but is not limited to humans, non-human primates, canines, felines, murines, bovines, equines, and porcines. In a particularly preferred embodiment, the term "mammal" refers to humans.

The term "nosocomial infection" refers to a hospital-acquired infection (HAI), which is an infection that is acquired in a hospital or other health care facility. To emphasize both hospital and nonhospital settings, it is sometimes instead called a health care-associated infection (HAI or HCAI). Such an infection can be acquired in hospitals, nursing homes, rehabilitation facilities, outpatient clinics, or other clinical settings.

Compounds of the Invention

In a first aspect, the present invention provides a compound of formula (I)

(I)

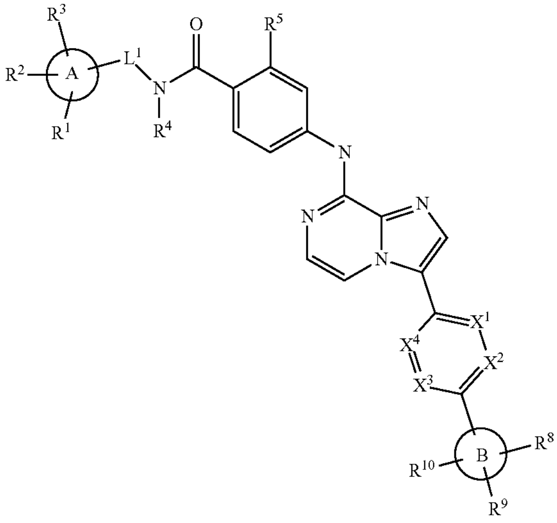

or a pharmaceutically acceptable salt thereof, wherein:

$X^1$ is N or C—$R^6$;

$X^2$ is N or C—$R^7$;

$X^3$ is N or C—$R^{11}$;

$X^4$ is N or C—$R^{12}$;

provided that at most one of $X^1$ to $X^4$ is N;

$R^1$, $R^2$, and $R^3$ are each independently selected from hydrogen, hydroxy, amino, halogen, cyano, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, carbamoyl-$C_1$-$C_6$-alkyl, carboxy-$C_1$-$C_6$-alkyl, $C_1$-$C_6$-alkoxy, halo-$C_1$-$C_6$-alkoxy, and a group

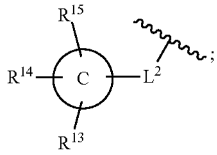

;

$R^4$ is hydrogen or $C_1$-$C_6$-alkyl;

$R^5$ is selected from hydrogen, halogen, cyano, $C_1$-$C_6$-alkyl, $C_1$-$C_6$-alkoxy, halo-$C_1$-$C_6$-alkyl, hydroxy-$C_1$-$C_6$-alkyl, and halo-$C_1$-$C_6$-alkoxy;

$R^6$, $R^7$, $R^{11}$, and $R^{12}$ are each independently selected from is hydrogen, hydroxy, amino, halogen, cyano, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, and halo-$C_1$-$C_6$-alkoxy;

$R^8$, $R^9$, and $R^{10}$ are each independently selected from hydrogen, halogen, cyano, amino, hydroxy, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl;

$R^{13}$, $R^{14}$, and $R^{15}$ are each independently selected from hydrogen, halogen, cyano, amino, hydroxy, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, and halo-$C_1$-$C_6$-alkoxy;

A and C are each independently a 3- to 14-membered heterocycle;

B is a 5- to 14-membered heteroaryl; and $L^1$ and $L^2$ are each independently selected from a covalent bond, carbonyl, and $C_1$-$C_6$-alkyldiyl.

In one embodiment, the present invention provides a compound of formula (I), or a pharmaceutically acceptable salt thereof, wherein the compound of formula (I) is a compound of formula (II):

(II)

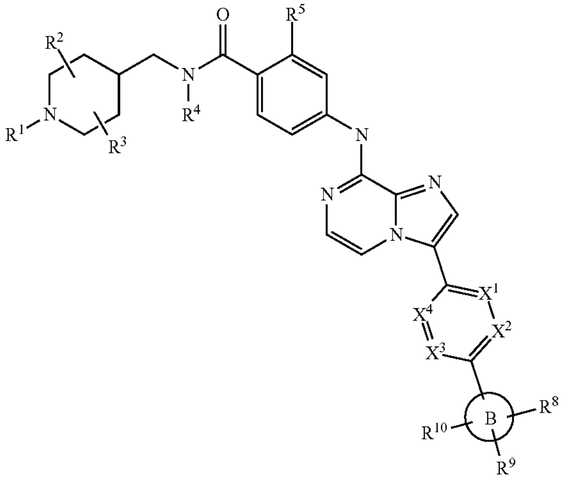

In one embodiment, the present invention provides a compound of formula (I), or a pharmaceutically acceptable salt thereof, wherein the compound of formula (I) is a compound of formula (III):

(III)

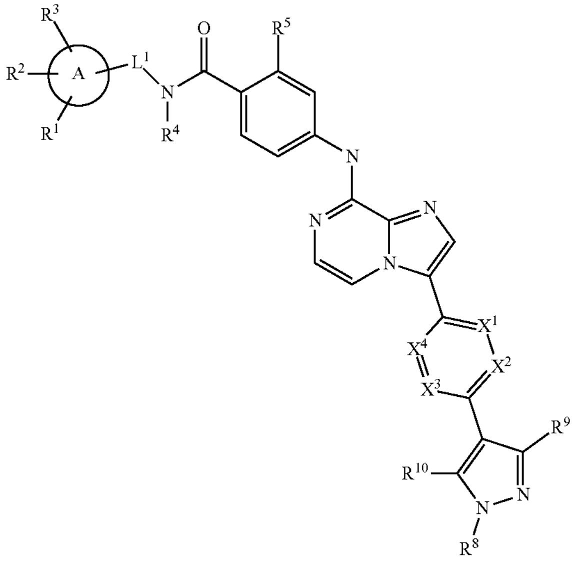

In one embodiment, the present invention provides a compound of formula (I), or a pharmaceutically acceptable salt thereof, wherein the compound of formula (I) is a compound of formula (IV):

(IV)

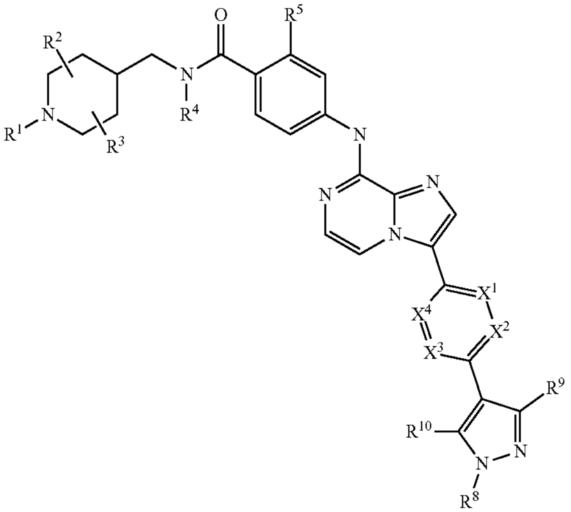

In one embodiment, the present invention provides a compound of formula (I) as described herein, or a pharmaceutically acceptable salt thereof, wherein:

$X^1$ is C—$R^6$.

In one embodiment, the present invention provides a compound of formula (I) as described herein, or a pharmaceutically acceptable salt thereof, wherein:

$X^2$ is N or C—$R^7$.

In one embodiment, the present invention provides a compound of formula (I) as described herein, or a pharmaceutically acceptable salt thereof, wherein:

$X^3$ is C—$R^{11}$.

In one embodiment, the present invention provides a compound of formula (I) as described herein, or a pharmaceutically acceptable salt thereof, wherein:

$X^4$ is C—$R^{12}$.

In one embodiment, the present invention provides a compound of formula (I) as described herein, or a pharmaceutically acceptable salt thereof, wherein:

$R^1$ is selected from hydrogen, $C_1$-$C_6$-alkyl, hydroxy-$C_1$-$C_6$-alkyl, carbamoyl-$C_1$-$C_6$-alkyl, carboxy-$C_1$-$C_6$-alkyl, and a group

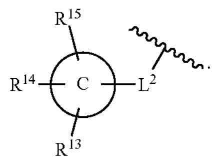

In a preferred embodiment, the present invention provides a compound of formula (I) as described herein, or a pharmaceutically acceptable salt thereof, wherein:

$R^1$ is a group

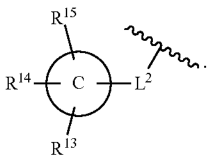

In one embodiment, the present invention provides a compound of formula (I) as described herein, or a pharmaceutically acceptable salt thereof, wherein:

$R^2$ is selected from hydrogen, $C_1$-$C_6$-alkyl, and carboxy-$C_1$-$C_6$-alkyl.

In a preferred embodiment, the present invention provides a compound of formula (I) as described herein, or a pharmaceutically acceptable salt thereof, wherein:

$R^2$ is selected from $C_1$-$C_6$-alkyl, and carboxy-$C_1$-$C_6$-alkyl.

In a particularly preferred embodiment, the present invention provides a compound of formula (I) as described herein, or a pharmaceutically acceptable salt thereof, wherein:

$R^2$ is selected from methyl, and carboxymethyl.

In one embodiment, the present invention provides a compound of formula (I) as described herein, or a pharmaceutically acceptable salt thereof, wherein:

$R^3$ is hydrogen.

In one embodiment, the present invention provides a compound of formula (I) as described herein, or a pharmaceutically acceptable salt thereof, wherein:

$R^4$ is hydrogen.

In one embodiment, the present invention provides a compound of formula (I) as described herein, or a pharmaceutically acceptable salt thereof, wherein:

$R^5$ is alkyl.

In a preferred embodiment, the present invention provides a compound of formula (I) as described herein, or a pharmaceutically acceptable salt thereof, wherein:

$R^5$ is ethyl.

In one embodiment, the present invention provides a compound of formula (I) as described herein, or a pharmaceutically acceptable salt thereof, wherein:

$R^6$ is hydrogen or halogen.

In a preferred embodiment, the present invention provides a compound of formula (I) as described herein, or a pharmaceutically acceptable salt thereof, wherein:

$R^6$ is halogen.

In a particularly preferred embodiment, the present invention provides a compound of formula (I) as described herein, or a pharmaceutically acceptable salt thereof, wherein:

$R^6$ is fluoro.

In one embodiment, the present invention provides a compound of formula (I) as described herein, or a pharmaceutically acceptable salt thereof, wherein:

$R^7$ is hydrogen or halogen.

In a preferred embodiment, the present invention provides a compound of formula (I) as described herein, or a pharmaceutically acceptable salt thereof, wherein:

$R^7$ is halogen.

In a particularly preferred embodiment, the present invention provides a compound of formula (I) as described herein, or a pharmaceutically acceptable salt thereof, wherein:

$R^7$ is fluoro.

In one embodiment, the present invention provides a compound of formula (I) as described herein, or a pharmaceutically acceptable salt thereof, wherein:

$R^8$ is selected from $C_1$-$C_6$-alkyl, halo-$C_1$-$C_6$-alkyl, cyano-$C_1$-$C_6$-alkyl, and $C_1$-$C_6$-alkoxy-$C_1$-$C_6$-alkyl.

In a preferred embodiment, the present invention provides a compound of formula (I) as described herein, or a pharmaceutically acceptable salt thereof, wherein:

$R^8$ is $C_1$-$C_6$-alkyl or $C_1$-$C_6$-alkoxy-$C_1$-$C_6$-alkyl.

In a particularly preferred embodiment, the present invention provides a compound of formula (I) as described herein, or a pharmaceutically acceptable salt thereof, wherein:

$R^8$ is methyl or 2-methoxyethyl.

In one embodiment, the present invention provides a compound of formula (I) as described herein, or a pharmaceutically acceptable salt thereof, wherein:

$R^9$ is hydrogen or $C_1$-$C_6$-alkyl.

In a preferred embodiment, the present invention provides a compound of formula (I) as described herein, or a pharmaceutically acceptable salt thereof, wherein:

$R^9$ is hydrogen or methyl.

In one embodiment, the present invention provides a compound of formula (I) as described herein, or a pharmaceutically acceptable salt thereof, wherein:

$R^{10}$ is hydrogen or $C_1$-$C_6$-alkyl.

In a preferred embodiment, the present invention provides a compound of formula (I) as described herein, or a pharmaceutically acceptable salt thereof, wherein:

$R^{10}$ is hydrogen or methyl.

In one embodiment, the present invention provides a compound of formula (I) as described herein, or a pharmaceutically acceptable salt thereof, wherein:

$R^{11}$ is hydrogen or halogen.

In a preferred embodiment, the present invention provides a compound of formula (I) as described herein, or a pharmaceutically acceptable salt thereof, wherein:

$R^{11}$ is hydrogen.

In one embodiment, the present invention provides a compound of formula (I) as described herein, or a pharmaceutically acceptable salt thereof, wherein:

$R^{12}$ is hydrogen or $C_1$-$C_6$-alkyl.

In a preferred embodiment, the present invention provides a compound of formula (I) as described herein, or a pharmaceutically acceptable salt thereof, wherein:

$R^{12}$ is hydrogen.

In one embodiment, the present invention provides a compound of formula (I) as described herein, or a pharmaceutically acceptable salt thereof, wherein:

$R^{13}$ is hydrogen.

In one embodiment, the present invention provides a compound of formula (I) as described herein, or a pharmaceutically acceptable salt thereof, wherein:

$R^{14}$ is hydrogen.

In one embodiment, the present invention provides a compound of formula (I) as described herein, or a pharmaceutically acceptable salt thereof, wherein:

$R^{15}$ is hydrogen.

In one embodiment, the present invention provides a compound of formula (I) as described herein, or a pharmaceutically acceptable salt thereof, wherein:

$L^1$ is $C_1$-$C_6$-alkyldiyl.

In a preferred embodiment, the present invention provides a compound of formula (I) as described herein, or a pharmaceutically acceptable salt thereof, wherein:

$L^1$ is $—CH_2—$.

In one embodiment, the present invention provides a compound of formula (I) as described herein, or a pharmaceutically acceptable salt thereof, wherein:

$L^2$ is $C_1$-$C_6$-alkyldiyl.

In a preferred embodiment, the present invention provides a compound of formula (I) as described herein, or a pharmaceutically acceptable salt thereof, wherein:

$L^2$ is —$CH_2$—.

In one embodiment, the present invention provides a compound of formula (I) as described herein, or a pharmaceutically acceptable salt thereof, wherein:

A is piperidyl.

In one embodiment, the present invention provides a compound of formula (I) as described herein, or a pharmaceutically acceptable salt thereof, wherein:

B is pyrazolyl.

In one embodiment, the present invention provides a compound of formula (I) as described herein, or a pharmaceutically acceptable salt thereof, wherein:

C is azetidinyl.

In one embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$;

$R^6$, $R^7$, and $R^{11}$ are each independently hydrogen or halogen; and $R^{12}$ is hydrogen or $C_1$-$C_6$-alkyl.

In a preferred embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$ $R^6$ and $R^7$ are halogen; and $R^{11}$ and $R^{12}$ are hydrogen.

In a particularly preferred embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$;

$R^6$ and $R^7$ are fluoro; and $R^{11}$ and $R^{12}$ are hydrogen.

In one embodiment, the present invention provides a compound of formula (I) as described herein, or a pharmaceutically acceptable salt thereof, wherein:

$R^1$ is selected from hydrogen, $C_1$-$C_6$-alkyl, hydroxy-$C_1$-$C_6$-alkyl, carbamoyl-$C_1$-$C_6$-alkyl, carboxy-$C_1$-$C_6$-alkyl, and a group

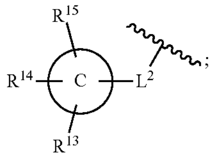

$R^2$ is selected from hydrogen, $C_1$-$C_6$-alkyl, and carboxy-$C_1$-$C_6$-alkyl;

$R^3$, $R^{13}$, $R^{14}$, and $R^{15}$ are hydrogen;

$L^1$ and $L^2$ are each independently $C_1$-$C_6$-alkyldiyl; and

A and C are each independently a 3- to 14-membered heterocycle.

In a preferred embodiment, the present invention provides a compound of formula (I) as described herein, or a pharmaceutically acceptable salt thereof, wherein:

$R^1$ is a group

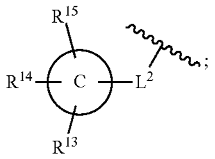

$R^2$ is $C_1$-$C_6$-alkyl or carboxy-$C_1$-$C_6$-alkyl;

$R^3$, $R^{13}$, $R^{14}$, and $R^{15}$ are hydrogen;

$L^1$ and $L^2$ are each independently $C_1$-$C_6$-alkyldiyl; and

A and C are each independently a 3- to 14-membered heterocycle.

In a particularly preferred embodiment, the present invention provides a compound of formula (I) as described herein, or a pharmaceutically acceptable salt thereof, wherein:

$R^1$ is a group

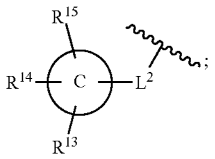

$R^2$ is methyl or carboxymethyl;

$R^3$, $R^{13}$, $R^{14}$, and $R^{15}$ are hydrogen;

$L^1$ and $L^2$ are —$CH_2$—;

A is piperidyl; and

C is azetidinyl.

In one embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$;

$R^1$ is selected from hydrogen, $C_1$-$C_6$-alkyl, hydroxy-$C_1$-$C_6$-alkyl, carbamoyl-$C_1$-$C_6$-alkyl, carboxy-$C_1$-$C_6$-alkyl, and a group

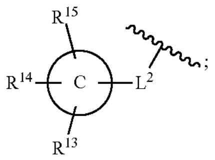

$R^2$ is selected from hydrogen, $C_1$-$C_6$-alkyl, and carboxy-$C_1$-$C_6$-alkyl;

$R^3$, $R^4$, $R^{13}$, $R^{14}$, and $R^{15}$ are hydrogen;

$R^5$ is $C_1$-$C_6$-alkyl;

$R^6$, $R^7$, and $R^{11}$ are each independently hydrogen or halogen;

$R^8$ is selected from $C_1$-$C_6$-alkyl, halo-$C_1$-$C_6$-alkyl, cyano-$C_1$-$C_6$-alkyl, and $C_1$-$C_6$-alkoxy-$C_1$-$C_6$-alkyl;

$R^9$, $R^{10}$, and $R^{12}$ are each independently hydrogen or $C_1$-$C_6$-alkyl;

A and C are each independently a 3- to 14-membered heterocycle;

B is a 5- to 14-membered heteroaryl; and $L^1$ and $L^2$ are each independently $C_1$-$C_6$-alkyldiyl.

In a preferred embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$;

$R^1$ is a group

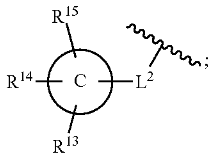

$R^2$ is $C_1$-$C_6$-alkyl or carboxy-$C_1$-$C_6$-alkyl;

$R^3$, $R^4$, $R^{11}$, $R^{12}$, $R^{13}$, $R^{14}$, and $R^{15}$ are hydrogen;

$R^5$ is $C_1$-$C_6$-alkyl;

$R^6$ and $R^7$ are halogen;

$R^8$ is $C_1$-$C_6$-alkyl or $C_1$-$C_6$-alkoxy-$C_1$-$C_6$-alkyl;

$R^9$ and $R^{10}$ are each independently hydrogen or $C_1$-$C_6$-alkyl;

A and C are each independently a 3- to 14-membered heterocycle;

B is a 5- to 14-membered heteroaryl; and $L^1$ and $L^2$ are each independently $C_1$-$C_6$-alkyldiyl.

In a particularly preferred embodiment, the present invention provides a compound of formula (I) as described herein, or a pharmaceutically acceptable salt thereof, wherein:

$X^1$ is C—$R^6$;

$X^2$ is N or C—$R^7$;

$X^3$ is C—$R^{11}$;

$X^4$ is C—$R^{12}$;

$R^1$ is a group

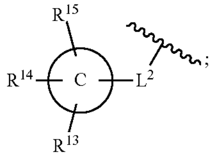

$R^2$ is methyl or carboxymethyl;

$R^3$, $R^4$, $R^{11}$, $R^{12}$, $R^{13}$, $R^{14}$, and $R^{15}$ are hydrogen;

$R^5$ is ethyl;

$R^6$ and $R^7$ are fluoro;

$R^8$ is methyl or 2-methoxyethyl;

$R^9$ and $R^{10}$ are each independently hydrogen or methyl;

A is piperidyl;

B is pyrazolyl;

C is azetidinyl; and $L^1$ and $L^2$ are —$CH_2$—.

In one embodiment, the present invention provides a compound of formula (I) as described herein, or a pharmaceutically acceptable salt thereof, wherein the compound of formula (I) is selected from:

N-[[1-(azetidin-3-ylmethyl)-4-piperidyl]methyl]-4-[[3-[2,3-difluoro-4-(3-methyl-1H-pyrazol-4-yl)phenyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide;

2-[1-(azetidin-3-ylmethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid;

2-[4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]-1-piperidyl]acetic acid;

2-[4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]-1-methyl-piperidin-1-ium-1-yl]acetic acid;

N-[[1-(azetidin-3-ylmethyl)-4-piperidyl]methyl]-4-[[3-[2,3-difluoro-4-[3-(trifluoromethyl)-1H-pyrazol-4-yl]phenyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-4-[[3-[2,3-difluoro-4-[3-(trifluoromethyl)-1H-pyrazol-4-yl]phenyl]imidazo[1,2-a]pyrazin-8-yl]amino]-2-ethyl-benzamide;

N-[[1-(2-amino-2-oxo-ethyl)-1-methyl-piperidin-1-ium-4-yl]methyl]-4-[[3-[4-[1-(cyanomethyl)-3-methyl-pyrazol-4-yl]-2,3-difluoro-phenyl]imidazo[1,2-a]pyrazin-8-yl]amino]-2-ethyl-benzamide;

N-[[1-(2-amino-2-oxo-ethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide;

2-[1-(2-amino-2-oxo-ethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid;

2-[1-(carboxymethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid;

N-[[1-(azetidin-3-ylmethyl)-4-piperidyl]methyl]-2-ethyl-4-[[3-[2-fluoro-6-(3-methyl-1H-pyrazol-4-yl)-3-pyridyl]imidazo[1,2-a]pyrazin-8-yl]amino]benzamide;

N-[[1-(azetidin-3-ylmethyl)-1-methyl-piperidin-1-ium-4-yl]methyl]-2-ethyl-4-[[3-[2-fluoro-6-(3-methyl-1H-pyrazol-4-yl)-3-pyridyl]imidazo[1,2-a]pyrazin-8-yl]amino]benzamide;

N-[[1-(azetidin-3-ylmethyl)-4-piperidyl]methyl]-4-[[3-[6-(3,5-dimethyl-1H-pyrazol-4-yl)-2-fluoro-3-pyridyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-4-[[3-[6-(3,5-dimethyl-1H-pyrazol-4-yl)-2-fluoro-3-pyridyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-2-ethyl-4-[[3-[5-fluoro-6-(3-methyl-1H-pyrazol-4-yl)-3-pyridyl]imidazo[1,2-a]pyrazin-8-yl]amino]benzamide;

N-[[1-(azetidin-3-ylmethyl)-1-methyl-piperidin-1-ium-4-yl]methyl]-2-ethyl-4-[[3-[4-methyl-6-(3-methyl-1H-pyrazol-4-yl)-3-pyridyl]imidazo[1,2-a]pyrazin-8-yl]amino]benzamide;

N-[[1-(azetidin-3-ylmethyl)-1-methyl-piperidin-1-ium-4-yl]methyl]-2-ethyl-4-[[3-[4-(3-methyl-1H-pyrazol-4-yl)phenyl]imidazo[1,2-a]pyrazin-8-yl]amino]benzamide;

4-[[3-[2,3-difluoro-4-(3-methyl-1H-pyrazol-4-yl)phenyl]imidazo[1,2-a]pyrazin-8-yl]amino]-2-ethyl-N-(4-piperidylmethyl)benzamide;

N-[[1-(azetidin-3-ylmethyl)-1-methyl-piperidin-1-ium-4-yl]methyl]-4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-benzamide;

N-[[1-(2-amino-2-oxo-ethyl)-1-methyl-piperidin-1-ium-4-yl]methyl]-4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-benzamide;

4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-N-[[1-(2-hydroxyethyl)-1-methyl-piperidin-1-ium-4-yl]methyl]benzamide;

4-[[3-[2,3-difluoro-4-[1-(2-methoxyethyl)-3-methyl-pyrazol-4-yl]phenyl]imidazo[1,2-a]pyrazin-8-yl]amino]-N-[(1,1-dimethylpiperidin-1-ium-4-yl)methyl]-2-ethyl-benzamide;

N-[[1-(2-amino-2-oxo-ethyl)-1-methyl-piperidin-1-ium-4-yl]methyl]-4-[[3-[2,3-difluoro-4-[1-(2-methoxyethyl)-3-methyl-pyrazol-4-yl]phenyl]imidazo[1,2-a]pyrazin-8-yl]amino]-2-ethyl-benzamide;

4-[[3-[2,3-difluoro-4-[1-(2-methoxyethyl)-3-methyl-pyrazol-4-yl]phenyl]imidazo[1,2-a]pyrazin-8-yl]amino]-2-ethyl-N-[[1-(2-hydroxyethyl)-1-methyl-piperidin-1-ium-4-yl]methyl]benzamide; and N-[[1-(azetidin-3-ylmethyl)-1-methyl-piperidin-1-ium-4-yl]methyl]-4-[[3-[2,3-difluoro-4-[1-(2-methoxyethyl)-3-methyl-pyrazol-4-yl]phenyl]imidazo[1,2-a]pyrazin-8-yl]amino]-2-ethyl-benzamide.

In a preferred embodiment, the present invention provides a compound of formula (I) as described herein, or a pharmaceutically acceptable salt thereof, wherein the compound of formula (I) is selected from:

N-[[1-(azetidin-3-ylmethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide;

2-[1-(azetidin-3-ylmethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid;

N-[[1-(azetidin-3-ylmethyl)-1-methyl-piperidin-1-ium-4-yl]methyl]-4-[[3-[6-(3,5-dimethyl-1H-pyrazol-4-yl)-2-fluoro-3-pyridyl]imidazo[1,2-a]pyrazin-8-yl]amino]-2-ethyl-benzamide; and N-[[1-(azetidin-3-ylmethyl)-1-methyl-piperidin-1-ium-4-yl]methyl]-4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-benzamide.

In one embodiment, the present invention provides pharmaceutically acceptable salts of the compounds of formula (I) as described herein, especially pharmaceutically acceptable salts selected from hydrochlorides, fumarates, lactates (in particular derived from L-(+)-lactic acid), tartrates (in particular derived from L-(+)-tartaric acid) and trifluoroacetates. In yet a further particular embodiment, the present invention provides compounds according to formula (I) as described herein (i.e., as "free bases" or "free acids", respectively).

In some embodiments, the compounds of formula (I) are isotopically-labeled by having one or more atoms therein replaced by an atom having a different atomic mass or mass number. Such isotopically-labeled (i.e., radiolabeled) compounds of formula (I) are considered to be within the scope of this disclosure. Examples of isotopes that can be incorporated into the compounds of formula (I) include isotopes of hydrogen, carbon, nitrogen, oxygen, phosphorous, sulfur, fluorine, chlorine, and iodine, such as, but not limited to, $^{2}H$, $^{3}H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. Certain isotopically-labeled compounds of formula (I), for example, those incorporating a radioactive isotope, are useful in drug and/or substrate tissue distribution studies. The radioactive isotopes tritium, i.e. $^{3}H$, and carbon-14, i.e., $^{14}C$, are particularly useful for this purpose in view of their ease of incorporation and ready means of detection. For example, a compound of formula (I) can be enriched with 1, 2, 5, 10, 25, 50, 75, 90, 95, or 99 percent of a given isotope.

Substitution with heavier isotopes such as deuterium, i.e. $^{2}H$, may afford certain therapeutic advantages resulting from greater metabolic stability, for example, increased in vivo half-life or reduced dosage requirements.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples as set out below using an appropriate isotopically-labeled reagent in place of the non-labeled reagent previously employed.

Processes of Manufacturing

The preparation of compounds of formula (I) of the present invention may be carried out in sequential or convergent synthetic routes. Syntheses of the compounds of the invention are shown in the following schemes. The skills required for carrying out the reactions and purifications of the resulting products are known to those skilled in the art. The substituents and indices used in the following description of the processes have the significance given hereinbefore unless indicated to the contrary. In more detail, the compounds of formula (I) can be manufactured by the methods given below, by the methods given in the examples or by analogous methods. Appropriate reaction conditions for the individual reaction steps are known to a person skilled in the art. Also, for reaction conditions described in literature affecting the described reactions see for example: *Comprehensive Organic Transformations: A Guide to Functional Group Preparations,* 3rd Edition, Richard C. Larock. John Wiley & Sons, New York, NY. 2018). We find it convenient to carry out the reactions in the presence or absence of a solvent. There is no particular restriction on the nature of the solvent to be employed, provided that it has no adverse effect on the reaction or the reagents involved and that it can dissolve the reagents, at least to some extent. The described reactions can take place over a wide range of temperatures, and the precise reaction temperature is not critical to the invention. It is convenient to carry out the described reactions in a temperature range between −78° C. to reflux temperature. The time required for the reaction may also vary widely, depending on many factors, notably the reaction temperature and the nature of the reagents. However, a period of from 0.5 h to several days will usually suffice to yield the described intermediates and compounds. The reaction sequence is not limited to the one displayed in the schemes, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Scheme 1

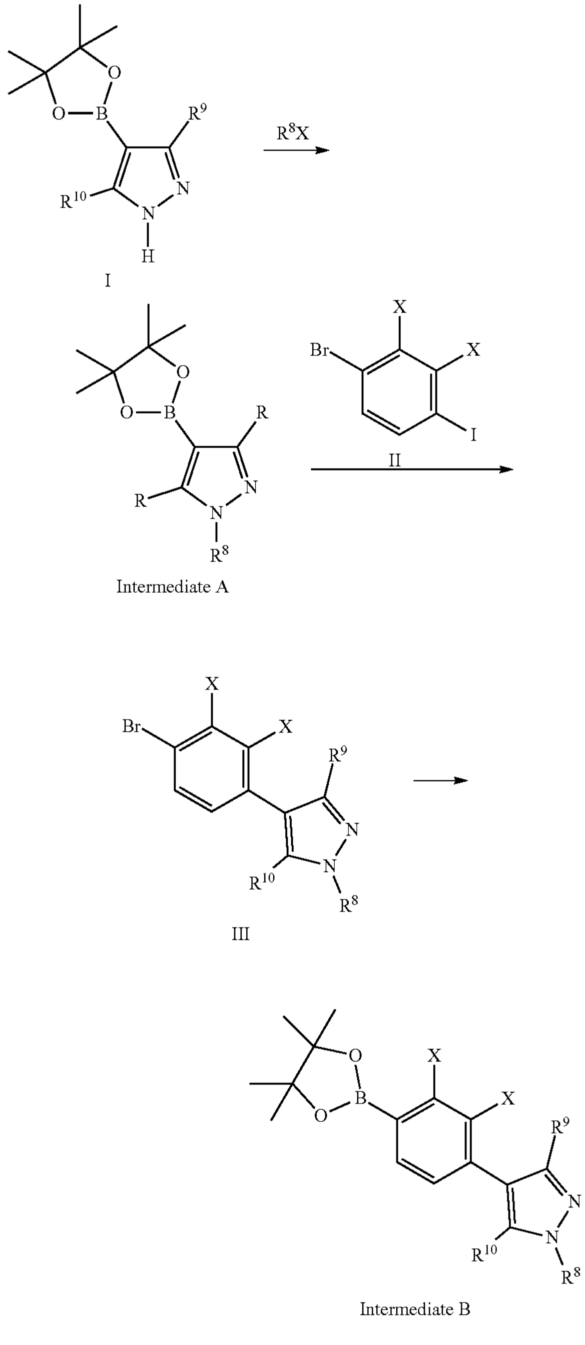

I

II

Intermediate A

III

Intermediate B wherein $R^9$ and $R^{10}$ are as defined herein, preferably H or Me;

X is halogen or H;

$R^8$ is as defined herein, preferably $C_{1-6}$alkyl, $C_{1-6}$alkoxy, or is a protective group, such as Boc or MOM.

Compound of Intermediate B can be prepared according to route in Scheme 1. Alkylation $R^8X$ with substituted pyrazole analogues (I) to give Intermediate A, which can couple with building block (II) to give Building block III. Bronic ester (Intermediate B) can be achieved using palladium catalysts and phosphine ligands then.

Scheme 2

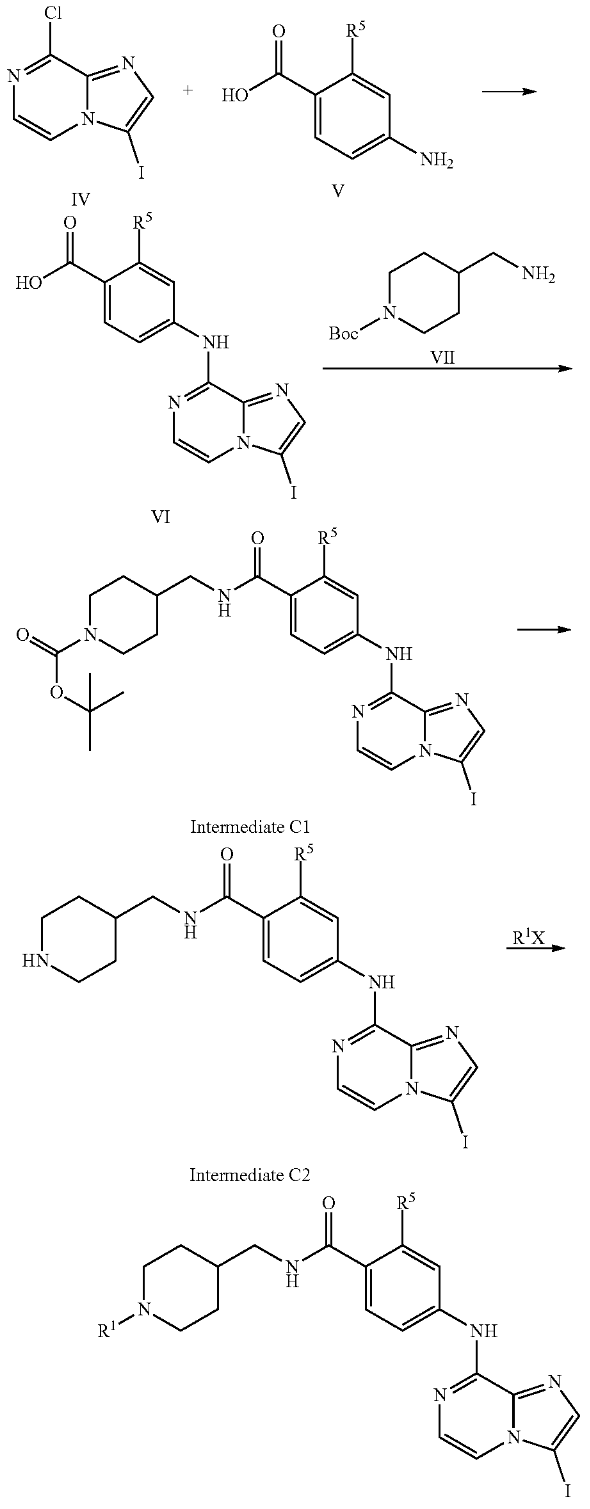

IV

V

VI

VII

Intermediate C1

Intermediate C2

Intermediate C wherein $R^5$ is as defined herein, preferably Me, Et or halogen;

$R^1$ is as defined herein, preferably $C_{1-6}$alkyl, $C_{1-6}$alkoxy, $C_{1-6}$amine or $C_{1-6}$aminocarbonyl, or is a protective group, such as Boc, MOM.

Compound of Intermediate C can be prepared according to route in Scheme 2. 8-chloro-3-iodo-imidazo[1,2-a]pyrazine (IV) can react with 4-aminobenzoic acid analogues (V) to give building block VI, which can couple with amine building block VII with condensing agent, such as HATU/DIPEA in DMSO to give the compound of formula Intermediate C1.

Remove protect group under acid condition to get Intermediate C2, which can be further be alkylated with $R^8X$ to get Intermediate C.

Scheme 3

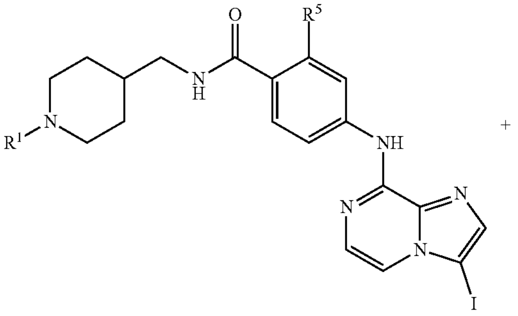

Intermediate C

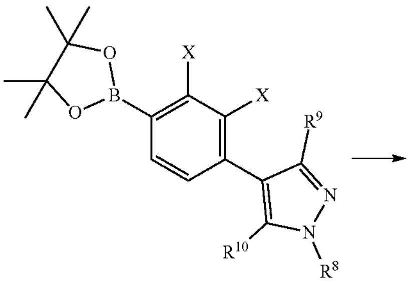

Intermediate B

-continued

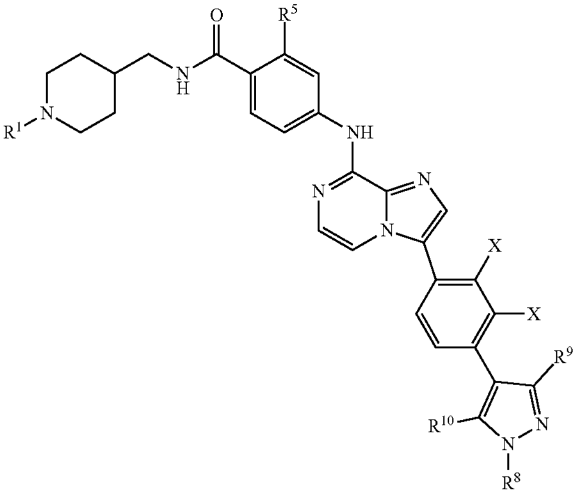

Intermediate D wherein $R^9$ and $R^{10}$ are as defined herein, preferably H or Me;

X is halogen or H;

$R^8$ is as defined herein, preferably $C_{1-6}$alkyl or $C_{1-6}$alkoxy, or is a protective group, such as Boc or MOM;

$R^1$ is as defined herein, preferably $C_{1-6}$alkyl, $C_{1-6}$alkoxy, $C_{1-6}$amine or $C_{1-6}$aminocarbonyl or is a protective group, such as Boc or MOM;

$R^5$ is as defined herein, preferably Me, Et or halogen.

Intermediate D can be prepared according to route in Scheme 3. Suziki coupling of Intermediate C with bronic ester (Intermediate B) can be achieved using palladium catalysts and phosphine ligands to give compound of formula Intermediate D.

Scheme 4

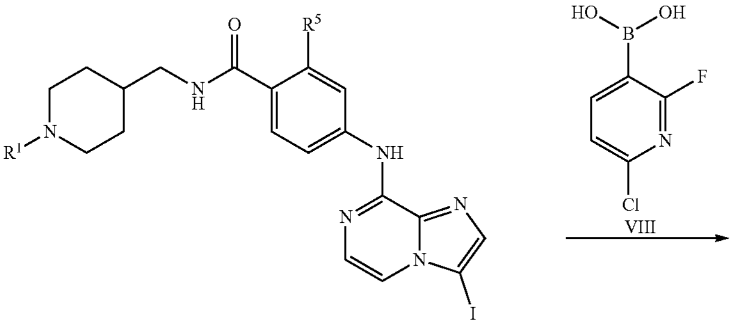

Intermediate C

-continued

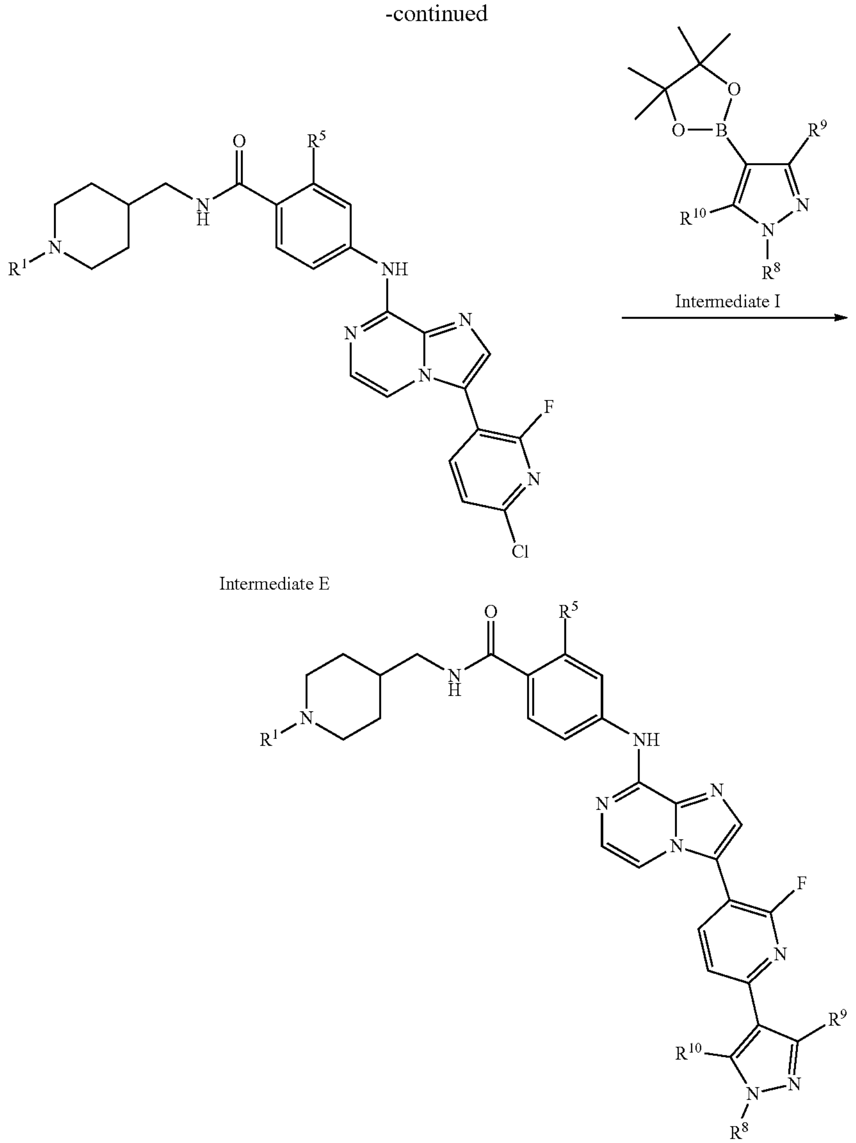

Intermediate E

Intermediate I

Intermediate F wherein $R^9$ and $R^{10}$ are as defined herein, preferably H or Me;

$R^8$ is as defined herein, preferably $C_{1-6}$alkyl or $C_{1-6}$alkoxy, or is a protective group, such as Boc or MOM;

$R^1$ is as defined herein, preferably $C_{1-6}$alkyl, $C_{1-6}$alkoxy, $C_{1-6}$amine or $C_{1-6}$aminocarbonyl or is a protective group, such as Boc or MOM;

$R^5$ is as defined herein, preferably Me, Et or halogen.

Intermediate F can be prepared according to route in Scheme 4. Suzuki coupling of Intermediate C with Aza-Aryl bronic ester (VIII) can be achieved using palladium catalysts and phosphine ligands to give compound of formula (Intermediate E). Then further Suzuki coupling of Intermediate I using classical palladium catalysts system to get compound of formula Intermediate F.

Scheme 5

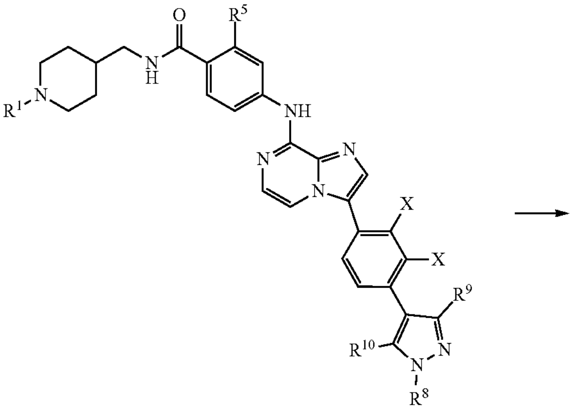

Intermediate D

-continued

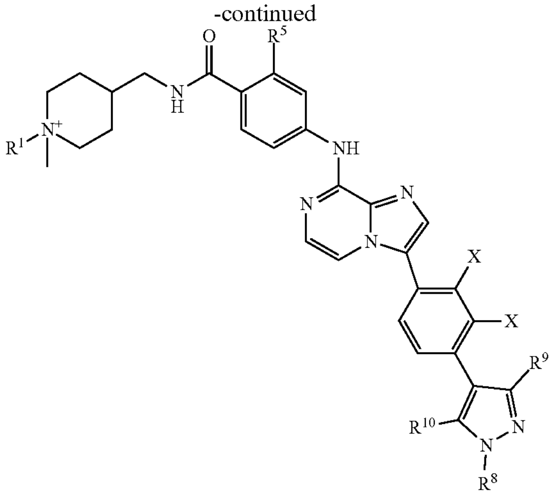

Example A-D

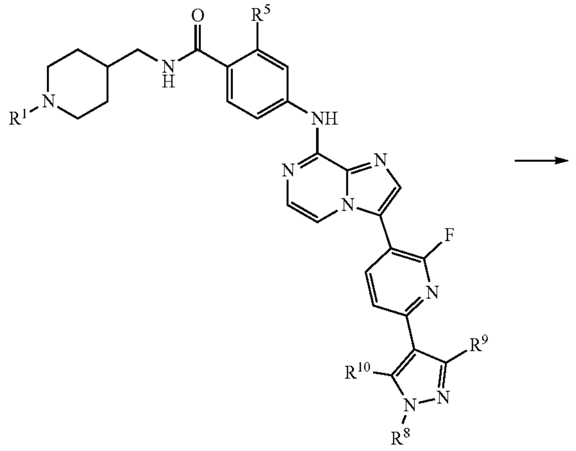

Intermediate F

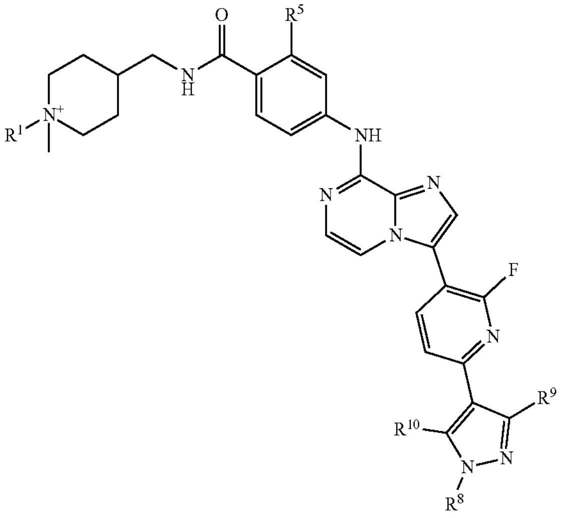

Example A-D wherein $R^9$ and $R^{10}$ are as defined herein, preferably H or Me;

X is halogen or H;

$R^8$ is as defined herein, preferably $C_{1-6}$alkyl or $C_{1-6}$alkoxy, or is a protective group, such as Boc or MOM;

$R^1$ is as defined herein, preferably $C_{1-6}$alkyl, $C_{1-6}$alkoxy, $C_{1-6}$amine or $C_{1-6}$aminocarbonyl or is a protective group, such as Boc or MOM;

$R^5$ is as defined herein, preferably Me, Et or halogen.

The Example A-D can be prepared according to the route in Scheme 5. The methylation of Intermediate D and Intermediate F can be achieved at mild conditions like MeI with DIPEA in acetonitrile at room temperature. The removal of the protective group can be before or after the methylation step, based on different substitution.

In one aspect, the present invention provides a process of manufacturing the compounds of formula (I) described herein, or pharmaceutically acceptable salts thereof, comprising:

(iii) Suzuki coupling of a heteroaryl halide C1, wherein $R^1$ to $R^5$, A, and $L^1$ are as defined herein and "Hal" is a halogen, preferably iodine, (C1)

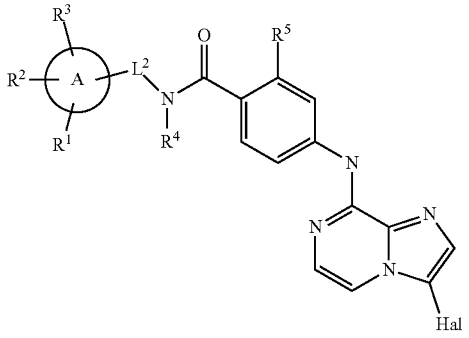

with a boronic acid (ester) B1, wherein $X^1$ to $X^4$, $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(B1)

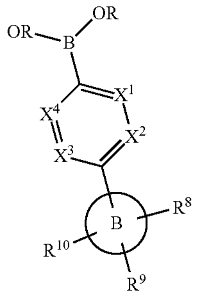

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I); or (iv) Suzuki coupling of an aryl/heteroaryl halide E1, wherein $R^1$ to $R^5$, A, $L^1$, and $X^1$ to $X^4$ are as defined herein and "Hal" is a halogen, preferably chlorine, (E1)

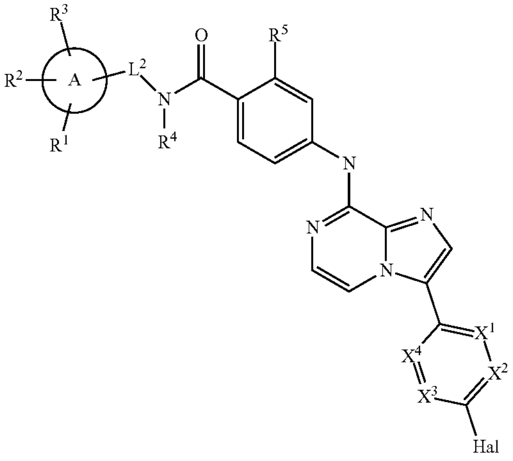

with a boronic acid (ester) I1, wherein $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(I1)

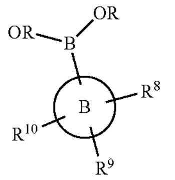

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I); to afford said compound of formula (I).

In a further aspect, the present invention provides a compound of formula (I) as described herein, or a pharmaceutically acceptable salt thereof, when manufactured according to the processes disclosed herein.

Using the Compounds

As illustrated in the experimental section, the compounds of formula (I) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii.*

The compounds of formula (I) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii.*

The compounds of formula (I) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii.*

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In one aspect, the present invention provides compounds of formula (I) or their pharmaceutically acceptable salts as described herein for use as therapeutically active substances.

In a further aspect, the present invention provides a compound of formula (I) as described herein, or a pharmaceutically acceptable salt thereof, for use as antibiotic.

In a further aspect, the present invention provides a compound of formula (I) as described herein, or a pharmaceutically acceptable salt thereof, for use in the treatment or prevention of nosocomial infections and resulting diseases.

In a particular embodiment, said nosocomial infections and resulting diseases are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by Gram-negative bacteria.

In a particular embodiment, said infections and resulting diseases caused by Gram-negative bacteria are selected from bacteremia, pneumonia, meningitis, urinary tract infection and wound infection, or a combination thereof.

In a further aspect, the present invention provides a compound of formula (I) as described herein, or a pharmaceutically acceptable salt thereof, for use in the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a preferred embodiment, the present invention provides a compound of formula (I) as described herein, or a pharmaceutically acceptable salt thereof, for use in the treatment or prevention of infections and resulting diseases caused by *Acinetobacter baumannii* or *Pseudomonas aeruginosa* or a combination thereof.

In a further preferred embodiment, the present invention provides a compound of formula (I) as described herein, or a pharmaceutically acceptable salt thereof, for use in the treatment or prevention of infections and resulting diseases caused by *Pseudomonas aeruginosa.*

In a further preferred embodiment, the present invention provides a compound of formula (I) as described herein, or a pharmaceutically acceptable salt thereof, for use in the treatment or prevention of infections and resulting diseases caused by *Acinetobacter baumannii.*

In a further aspect, the present invention provides a method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, which method comprises administering a compound of formula (I) as described herein, or a pharmaceutically acceptable salt thereof, to a mammal.

In a further aspect, the present invention provides the use of a compound of formula (I) as described herein, or a pharmaceutically acceptable salt thereof, as an antibiotic.

In a further aspect, the present invention provides the use of a compound of formula (I) as described herein, or a pharmaceutically acceptable salt thereof, for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a further aspect, the present invention provides the use of a compound of formula (I) as described herein, or a pharmaceutically acceptable salt thereof, for the preparation of medicaments useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In a particular embodiment, said infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, are selected from bacteremia, pneumonia, meningitis, urinary tract infection and wound infection, or a combination thereof.

In a further aspect, the present invention provides compounds of formula (I) or their pharmaceutically acceptable salts as defined above for use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering a compound of formula (I) or a pharmaceutically acceptable salt thereof as defined above to a mammal.

In a further aspect, the present invention provides the use of compounds of formula (I) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

In a further aspect, the present invention provides the use of compounds of formula (I) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I) or their pharmaceutically acceptable salts as defined above.

Pharmaceutical Compositions and Administration

In one aspect, the present invention provides pharmaceutical compositions comprising compounds of formula (I) or their pharmaceutically acceptable salts as defined above and one or more pharmaceutically acceptable excipients. Exemplary pharmaceutical compositions are described in Examples 1 to 4.

In a further aspect, the present invention relates to pharmaceutical compositions comprising compounds of formula (I) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii.*

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions or infusion solutions).

The compounds of formula (I) and their pharmaceutically acceptable salts can be processed with pharmaceutically inert, inorganic or organic excipients for the production of tablets, coated tablets, dragées and hard gelatin capsules. Lactose, corn starch or derivatives thereof, talc, stearic acid or its salts etc. can be used, for example, as such excipients for tablets, dragées and hard gelatin capsules.

Suitable excipients for soft gelatin capsules are, for example, vegetable oils, waxes, fats, semi-solid substances and liquid polyols, etc.

Suitable excipients for the production of solutions and syrups are, for example, water, polyols, saccharose, invert sugar, glucose, etc.

Suitable excipients for injection solutions are, for example, water, alcohols, polyols, glycerol, vegetable oils, etc.

Suitable excipients for suppositories are, for example, natural or hardened oils, waxes, fats, semi-solid or liquid polyols, etc.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should be appropriate. It will, however, be clear that the upper limit given herein can be exceeded when this is shown to be indicated.

Co-Administration of Compounds of Formula (I) and Other Agents

The compounds of formula (I) or salts thereof or a compound disclosed herein or a pharmaceutically acceptable salt thereof may be employed alone or in combination with other agents for treatment. For example, the second agent of the pharmaceutical combination formulation or dosing regimen may have complementary activities to the compound of formula (I) such that they do not adversely affect each other. The compounds may be administered together in a unitary pharmaceutical composition or separately. In one embodiment a compound or a pharmaceutically acceptable salt can be co-administered with an antibiotic, in particular with an antibiotic for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

The term “co-administering” refers to either simultaneous administration, or any manner of separate sequential administration, of a compound of formula (I) or a salt thereof or a compound disclosed herein or a pharmaceutically acceptable salt thereof and a further active pharmaceutical ingredient or ingredients, including antibiotic agents. If the administration is not simultaneous, the compounds are administered in a close time proximity to each other. Furthermore, it does not matter if the compounds are administered in the same dosage form, e.g. one compound may be administered intravenously and another compound may be administered orally.

Typically, any agent that has antimicrobial activity may be co-administered. Particular examples of such agents are Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified e.g. in WO 2017072062 A1, WO 2019185572 A1 and WO 2019206853 A1, and Macrolides (erythromycin).

In one aspect, the present invention provides a pharmaceutical composition described herein, further comprising an additional therapeutic agent.

In one aspect, the present invention provides a pharmaceutical combination comprising a compound of formula (I) described herein and an additional therapeutic agent.

In one embodiment, said additional therapeutic agent is an antibiotic agent.

In one embodiment, said additional therapeutic agent is an antibiotic agent that is useful for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof.

In one embodiment, said additional therapeutic agent is an antibiotic agent selected from Carbapenems (meropenem), Fluoroquinolone (Ciprofloxacin), Aminoglycoside (amikacin), Tetracyclines (tigecycline), Colistin, Sulbactam, Sulbactam+Durlobactam, Cefiderocol (Fetroja), macrocyclic peptides as exemplified in WO 2017072062 A1, WO 2019185572 A1 and WO 2019206853 A1, and Macrolides (erythromycin).

EXAMPLES

The invention will be more fully understood by reference to the following examples. The claims should not, however, be construed as limited to the scope of the examples.

In case the preparative examples are obtained as a mixture of enantiomers, the pure enantiomers can be separated by methods described herein or by methods known to the man skilled in the art, such as e.g., chiral chromatography (e.g., chiral SFC) or crystallization.

All reaction examples and intermediates were prepared under an argon atmosphere if not specified otherwise.

Abbreviations used herein are as follows:

ACN or MeCN acetonitrile
BINAP 2,2'-Bis(diphenylphosphino)-1,1'-binaphthalene
CFU colony-forming unit
d day
DCM dichloromethane
DIPEA N,N-diisopropylethylamine
EtOAc or EA ethyl acetate
FA formic acid
h(s) or hr(s) hour
HATU: 1-[Bis(dimethylamino)methylene]-1H-1,2,3-triazolo[4,5-b]pyridinium 3-oxid hexafluorophosphate
HPLC: high performance liquid chromatography
HPLC-UV: high performance liquid chromatography with ultraviolet detector
IC50 half maximal inhibitory concentration
IC90 90% inhibitory concentration
PE petroleum ether
$PdCl_2$(DPPF) 1,1'-Bis(diphenylphosphino)ferrocene]dichloropalladium(II)
$Pd_2(dba)_3$ Tris(dibenzylideneacetone)dipalladium(0)
PG Protect group
Precat precatalyst
prep-HPLC preparative high performance liquid chromatography
rt room temperature
sat saturated
SEM 2-methoxyethyl(trimethyl)silane
FA Formic acid
TFA Trifluoroacetic Acid
wt weight
X-PHOS 2-Dicyclohexylphosphino-2',4',6'-triisopropylbiphenyl

Intermediate A1

1-(2-Methoxyethyl)-3-methyl-4-(4,4,5,5-tetramethyl-1,3,2-dioxaborolan-2-yl)pyrazole To a 25 mL microwave vial was added 3-methyl-4-(4.4.5.5-tetramethyl-1, 3, 2-dioxaborolan-2-yl)-1H-pyrazole (2 g, 9.61 mmol), 1-bromo-2-methoxyethane (1.74 g, 12.5 mmol), $K_2CO_3$ (1.73 g, 12.5 mmol) and potassium iodide (319 mg, 1.92 mmol) in DMF (15 mL). The vial capped and heated in the microwave at 100° C. for 15 h. The reaction mixture filtered through glass fiber paper. The filtrate was concentrated in vacuum. The crude material purified by flash chromatography (silica gel, 40 g, 10% to 40% EtOAc in hexanes) to afford 2 g of crude product, the crude product was purified by preparative HPLC. to afford 1-(2-methoxyethyl)-3-methyl-4-(4,4,5,5-tetramethyl-1,3,2-dioxaborolan-2-yl)pyrazole (550 mg, 2.07 mmol, 21.5% yield) and 1-(2-methoxyethyl)-5-methyl-4-(4,4,5,5-tetramethyl-1,3,2-dioxaborolan-2-yl)pyrazole (316 mg, 1.19 mmol, 12.4% yield). MS $[M+H]^+$: 280.3.

Intermediate A2

1-(2-Methoxyethyl)-3,5-dimethyl-4-(4,4,5,5-tetramethyl-1,3,2-dioxaborolan-2-yl)pyrazole To a 25 mL microwave vial was added 3, 5-dimethyl-4-(4, 4, 5, 5-tetramethyl-1, 3, 2-dioxaborolan-2-yl)-1H-pyrazole (2 g, 9.01 mmol), 1-bromo-2-methoxyethane (1.63 g, 11.7 mmol), $K_2CO_3$ (1.62 g, 11.7 mmol) and potassium iodide (299 mg, 1.8 mmol) in DMF (15 mL). The vial capped and heated in the microwave at 100° C. for 15 h. The reaction mixture filtered through glass fiber paper. The filtrate was concentrated in vacuum. The crude material purified by flash chromatography (silica gel, 40 g, 10% to 40% EtOAc in hexanes), to afford 1-(2-methoxyethyl)-3,5-dimethyl-4-(4,4,5,5-tetramethyl-1,3,2-dioxaborolan-2-yl)pyrazole (1.5 g, 5.35 mmol, 59.5% yield). MS $[M+H]^+$: 281.1.

Intermediate A3

Trimethyl-[2-[[3-methyl-4-(4,4,5,5-tetramethyl-1,3,2-dioxaborolan-2-yl)pyrazol-1-yl]methoxy]ethyl]silane In a 100 mL round-bottomed flask, 3-methyl-4-(4,4,5,5-tetramethyl-1,3,2-dioxaborolan-2-yl)-1H-pyrazole (1.5 g, 7.21 mmol), SEM-Cl (1.56 g, 1.66 mL, 9.37 mmol) and DIPEA (2.8 g, 3.78 mL, 21.6 mmol) were combined with DCM (30 mL) to give a colorless solution. The reaction stirred at room temperature for 2 h. The crude reaction mixture was concentrated in vacuum. The crude material purified by flash chromatography (silica gel, 40 g, 0% to 30% DCM in PE). To afford trimethyl-[2-[[3-methyl-4-(4,4,5,5-tetramethyl-1,3,2-dioxaborolan-2-yl)pyrazol-1-yl]methoxy]ethyl]silane (2.4 g, 98.4% yield). MS$[M+H]^+$: 339.4.

Intermediate B1

2-[[4-[2,3-Difluoro-4-(4,4,5,5-tetramethyl-1,3,2-dioxaborolan-2-yl)phenyl]-3-methyl-pyrazol-1-yl]methoxy]ethyl-trimethyl-silane Step 1: 2-[[4-(4-bromo-2,3-difluoro-phenyl)-3-methyl-pyrazol-1-yl]methoxy]ethyl-trimethyl-silane To a 25 mL microwave vial was added 3-methyl-4-(4,4,5,5-tetramethyl-1,3,2-dioxaborolan-2-yl)-1-((2-(trimethylsilyl)ethoxy)methyl)-1H-pyrazole (1 g, 2.96 mmol), 1,4-dibromo-2,3-difluorobenzene (1.61 g, 5.91 mmol), 1,1'-bis(di-tert-butylphosphino)ferrocene palladium dichloride (193 mg, 296 μmol) and $Na_2CO_3$ (940 mg, 8.87 mmol) in dioxane (15 mL)/water (1.5 mL). The vial capped and heated at 100° C. for 2 h under $N_2$. The reaction mixture filtered through glass fiber paper. The filtrate was concentrated in vacuum. The crude material was purified by flash chromatography (silica gel, 40 g, 25% to 80% DCM in PE), to afford 2-[[4-(4-bromo-2,3-difluoro-phenyl)-3-methyl-pyrazol-1-yl]methoxy]ethyl-trimethyl-silane(324 mg, 803 μmol, 27.2% yield). MS $[M+H]^+$: 405.1.

Step 2: 2-[[4-[2,3-difluoro-4-(4,4,5,5-tetramethyl-1,3,2-dioxaborolan-2-yl)phenyl]-3-methyl-pyrazol-1-yl]methoxy]ethyl-trimethyl-silane In a 100 mL round-bottomed flask, bis(pinacolato)diboron (265 mg, 1.04 mmol), 4-(4-bromo-2,3-difluorophenyl)-3-methyl-1-((2-(trimethylsilyl)ethoxy)methyl)-1H-pyrazole (324 mg, 803 μmol), $PdCl_2(dppf)-CH_2Cl_2$ adduct (58.8 mg, 80.3 μmol) and potassium acetate (237 mg, 2.41 mmol) combined with dioxane (10 mL) to give a dark red solution. The reaction mixture heated to 80° C. and stirred for 15 h under $N_2$. The crude reaction mixture was concentrated in vacuum. The crude material purified by flash chromatography (silica gel, 40 g, 30% to 80% PE in DCM). to afford 2-[[4-[2,3-difluoro-4-(4,4,5,5-tetramethyl-1,3,2-dioxaborolan-2-yl)phenyl]-3-methyl-pyrazol-1-yl]methoxy]ethyl-trimethyl-silane (350 mg, 777 μmol, 96.7% yield). MS $[M+H]^+$: 451.3.

The following intermediates were prepared in analogy:

| Int. | Name | MS ESI $[M + H]^+$ | Starting Material |
|---|---|---|---|
| Intermediate B2 | 3-methyl-4-[4-(4,4,5,5-tetramethyl-1,3,2-dioxaborolan-2-yl)phenyl]-1H-pyrazole | 285.9 | 1-bromo-4-iodobenzene and 3-methyl-4-(4,4,5,5-tetramethyl-1,3,2-dioxaborolan-2-yl)-1H-pyrazole; $B_2pin_2$ |
| Intermediate B3 | 4-[2,3-difluoro-4-(4,4,5,5-tetramethyl-1,3,2-dioxaborolan-2-yl)phenyl]-3-methyl-1H-pyrazole | 321.2 | 1-bromo-2,3-difluoro-4-iodobenzene and 3-methyl-4-(4,4,5,5-tetramethyl-1,3,2-dioxaborolan-2-yl)-1H-pyrazole; $B_2pin_2$ |
| Intermediate B4 | 4-(2,3-difluoro-4-(4,4,5,5-tetramethyl-1,3,2-dioxaborolan-2-yl)phenyl)-3-(trifluoromethyl)-1H-pyrazole | 375.3 | 1-bromo-2,3-difluoro-4-iodobenzene and 4-(4,4,5,5-tetramethyl-1,3,2-dioxaborolan-2-yl)-3-(trifluoromethyl)-1H-pyrazole; $B_2pin_2$ |
| Intermediate B5 | 4-[2,3-difluoro-4-(4,4,5,5-tetramethyl-1,3,2-dioxaborolan-2-yl)phenyl]-1-(2-methoxyethyl)-3,5-dimethyl-pyrazole | 393.2 | 1-bromo-2,3-difluoro-4-iodobenzene and intermediate A2; $B_2pin_2$ |
| Intermediate B6 | 4-[2,3-difluoro-4-(4,4,5,5-tetramethyl-1,3,2-dioxaborolan-2-yl)phenyl]-1-(2-methoxyethyl)-3-methyl-pyrazole | 379.3 | 1-bromo-2,3-difluoro-4-iodobenzene and intermediate A1; $B_2pin_2$ |

Intermediates C1 & C2 tert-Butyl 4-[[[2-ethyl-4-[(3-odoimidazo[1,2-a]pyrazin-8-yl)amino]benzoyl]amino]methyl]piperidine-1-carboxylate (Intermediate C1)

2-Ethyl-4-[(3-iodoimidazo[1,2-a]pyrazin-8-yl)amino]-N-(4-piperidylmethyl)benzamide (Intermediate C2)

Step 1: 2-ethyl-4-[(3-iodoimidazo[1,2-a]pyrazin-8-yl)amino]benzoic acid

4-Amino-2-ethylbenzoic acid (3 g, 18.2 mmol) and 8-chloro-3-iodoimidazo[1,2-a]pyrazine (5.33 g, 19.1 mmol) was suspended in MeCN (33 mL) and AcOH (3.3 mL). The mixture heated in a sealed microwave tube at 100° C. for 18 h, and then cooled to room temperature. The precipitate collected by filtration and washed with ether (30 mL×3). The cake was dried in vacuum to afford the product 2-ethyl-4-((3-iodoimidazo[1,2-a]pyrazin-8-yl)amino)benzoic acid (7.08 g, 95.5% yield).

Step 2: tert-butyl 4-((2-ethyl-4-((3-iodoimidazo[1,2-a]pyrazin-8-yl)amino)benzamido) methyl)piperidine-1-carboxylate In a 50 mL round-bottomed flask, 2-ethyl-4-((3-iodoimidazo[1,2-a]pyrazin-8-yl)amino)benzoic acid (287 mg, 703 μmol), tert-butyl 4-(aminomethyl)piperidine-1-carboxylate (196 mg, 914 μmol), HATU (348 mg, 914 μmol) and DIPEA (273 mg, 368 μl, 2.11 mmol) were combined with DMF (5 mL) to give a light brown solution. The reaction stirred at room temperature for 30 min. The reaction mixture was poured into 25 mL $H_2O$ and extracted with EtOAc (25 mL×3). Combined the organic, washed with sat. NaCl (25 mL), dried over $Na_2SO_4$ and concentrated in vacuum. The crude material purified by flash chromatography (silica gel, 12 g, 0% to 5% MeOH in DCM) to afford tert-butyl 4-((2-ethyl-4-((3-iodoimidazo[1,2-a]pyrazin-8-yl)amino)benzamido)methyl)piperidine-1-carboxylate (363 mg, 601 μmol, 85.4% yield). MS $[M+H]^+$: 605.4.

Step 3: 2-ethyl-4-[(3-iodoimidazo[1,2-a]pyrazin-8-yl)amino]-N-(4-piperidylmethyl) benzamide In a 50 mL round-bottomed flask, tert-butyl 4-((2-ethyl-4-((3-iodoimidazo[1,2-a]pyrazin-8-yl)amino)benzamido)methyl)piperidine-1-carboxylate (240 mg, 397 μmol) was combined with THE (4 mL) to give a light yellow solution. HCl (in water) (1.65 mL, 19.9 mmol) was added. The reaction stirred at room temperature for 1 h. The crude reaction mixture was concentrated in vacuum. The crude product was directly used to the next step to afford 2-ethyl-4-[(3-iodoimidazo[1,2-a]pyrazin-8-yl)amino]-N-(4-piperidylmethyl)benzamide (200 mg, 397 μmol, 99.9% yield). MS $[M+H]^+$: 505.0

Intermediate C3 tert-Butyl3-[[4-[[[2-ethyl-4-[(3-iodoimidazo[1,2-a]pyrazin-8-yl)amino]benzoyl]amino]methyl]-1-piperidyl]methyl]azetidine-1-carboxylate In a 100 mL round-bottomed flask, 2-ethyl-4-((3-iodoimidazo[1,2-a]pyrazin-8-yl)amino)-N-(piperidin-4-ylmethyl) benzamide (200 mg, 397 μmol), tert-butyl 3-formylazetidine-1-carboxylate (220 mg, 1.19 mmol) and $NaBH_3CN$ (125 mg, 1.98 mmol) were combined with MeOH (10 mL) to give a light brown solution. The reaction mixture heated to 45° C. and stirred for 3 h. The crude reaction mixture was concentrated in vacuum. The reaction mixture was poured into 25 mL $H_2O$ and extracted with EtOAc (25 mL×3). Combined the organic layers were, washed with sat. NaCl (25 mL), dried over $Na_2SO_4$ and concentrated in vacuum to afford tert-butyl 3-[[4-[[[2-ethyl-4-[(3-iodoimidazo[1,2-a]pyrazin-8-yl)amino]benzoyl]amino]methyl]-1-piperidyl]methyl]azetidine-1-carboxylate (160 mg, 238 μmol, 59.9% yield). MS $[M+H]^+$: 674.2.

Intermediate C4 tert-Butyl 2-[4-[[[2-ethyl-4-[(3-iodoimidazo[1,2-a]pyrazin-8-yl)amino]benzoyl]amino]methyl]-1-piperidyl]acetate In a 50 mL round-bottomed flask, 2-ethyl-4-((3-iodoimidazo[1,2-a]pyrazin-8-yl)amino)-N-(piperidin-4-ylmethyl) benzamide (120 mg, 238 μmol) and DIPEA (40 mg, 54 μl, 309 μmol) were combined with DMF (3 mL) to give a light brown solution, tert-butyl 2-bromoacetate (60.3 mg, 309 μmol) added. The reaction stirred at room temperature for 1 h. The reaction mixture was poured into 25 mL $H_2O$ and extracted with EtOAc (25 mL×3). The organic layers were combined, washed with sat NaCl (25 mL). The organic layers were dried over $Na_2SO_4$ and concentrated in vacuum to afford tert-butyl 2-[4-[[[2-ethyl-4-[(3-iodoimidazo[1,2-a]pyrazin-8-yl)amino]benzoyl]amino]methyl]-1-piperidyl]acetate (112 mg, 181 μmol, 76.1% yield). MS $[M+H]^+$: 619.2.

Intermediate C5

N-[[1-(2-Amino-2-oxo-ethyl)-4-piperidyl]methyl]-2-ethyl-4-[(3-iodoimidazo[1,2-a]pyrazin-8-yl)amino]benzamide In a 50 mL round-bottomed flask, 2-ethyl-4-((3-iodoimidazo[1,2-a]pyrazin-8-yl)amino)-N-(piperidin-4-ylmethyl) benzamide (140 mg, 278 μmol) and DIPEA (46.6 mg, 63 μl, 361 μmol) were combined with DMF (3 mL) to give a light brown solution. 2-iodoacetamide (56.5 mg, 305 μmol) was added. The reaction stirred at room temperature for 1 h. The reaction mixture was poured into 25 mL $H_2O$ and extracted with EtOAc (25 mL×3). The organic layers were combined, washed with sat NaCl (25 mL). The organic layers dried over $Na_2SO_4$ and concentrated in vacuum. The crude material purified by flash chromatography (silica gel, 12 g, 0% to 10% MeOH in DCM) to afford N-[[1-(2-amino-2-oxo-ethyl)-4-piperidyl]methyl]-2-ethyl-4-[(3-iodoimidazo[1,2-a]pyrazin-8-yl)amino]benzamide (112 mg, 199 μmol, 71.9% yield). MS$[M+H]^+$: 562.2.

Intermediate D1 tert-Butyl 3-[[4-[[[4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzoyl]amino]methyl]-1-piperidyl]methyl]azetidine-1-carboxylate To a 25 mL microwave vial, tert-butyl 3-((4-((2-ethyl-4-((3-iodoimidazo[1,2-a]pyrazin-8-yl)amino)benzamido)methyl)piperidin-1-yl)methyl)azetidine-1-carboxylate (75 mg, 111 μmol), 4-(2,3-difluoro-4-(4, 4, 5, 5-tetramethyl-1, 3, 2-dioxaborolan-2-yl)phenyl)-3-methyl-1-((2-(trimethylsilyl)ethoxy)methyl)-1H-pyrazole (100 mg, 223 μmol), $PdCl_2$ (dppf)-$CH_2Cl_2$ adduct (8.15 mg, 11.1 μmol) and $Na_2CO_3$ (35.4 mg, 334 μmol) was added with Dioxane (10 mL)/Water (1 mL). The vial capped and heated at 100° C. for 2 h under $N_2$. The crude reaction mixture concentrated in vacuum. The crude material purified by flash chromatography (silica gel, 40 g, 0% to 10% MeOH in DCM) to afford tert-butyl 3-[[4-[[[4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzoyl]amino]methyl]-1-piperidyl]methyl]azetidine-1-carboxylate (39 mg, 44.8 μmol, 40.3% yield). MS $[M+H]^+$: 870.6.

The following intermediates were prepared in analogy:

| Int. | Name | MS ESI $[M + H]^+$ | Starting Material |
|---|---|---|---|
| Intermediate D2 | N-[[1-(2-amino-2-oxo-ethyl)-4-piperidyl]methyl]-4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzamide | 772.8 | Intermediate B1; Intermediate C5 |
| Intermediate D3 | tert-butyl 3-[[4-[[[4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzoyl]amino]methyl]-1-piperidyl]methyl]azetidine-1-carboxylate | 870.6 | Intermediate B1; Intermediate C3 |
| Intermediate D4 | tert-butyl 2-[4-[[[4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzoyl]amino]methyl]-1-piperidyl]acetate | 815.7 | Intermediate B1; Intermediate C4 |
| Intermediate D5 | tert-butyl 4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidine-1-carboxylate | 671.6 | Intermediate B3; Intermediate C1 |
| Intermediate D6 | tert-butyl 4-((4-((3-(2,3-difluoro-4-(1-(2-methoxyethyl)-3-methyl-1H-pyrazol-4-yl)phenyl)imidazo[1,2-a]pyrazin-8-yl)amino)-2-ethylbenzamido)methyl)piperidine-1-carboxylate | 729.4 | Intermediate B6; Intermediate C1 |
| Intermediate D7 | tert-butyl 4-((4-((3-(2,3-difluoro-4-(1-(2-methoxyethyl)-3,5-dimethyl-1H-pyrazol-4-yl)phenyl)imidazo[1,2-a]pyrazin-8-yl)amino)-2-ethylbenzamido)methyl)piperidine-1-carboxylate | 743.5 | Intermediate B5; Intermediate C1 |
| Intermediate D8 | tert-butyl 3-((4-((2-ethyl-4-((3-(4-(3-methyl-1H-pyrazol-4-yl)phenyl)imidazo[1,2-a]pyrazin-8-yl)amino)benzamido)methyl)piperidin-1-yl)methyl)azetidine-1-carboxylate | 704.9 | Intermediate B2; Intermediate C3 |
| Intermediate D9 | tert-butyl 3-((4-((4-((3-(2,3-difluoro-4-(3-(trifluoromethyl)-1H-pyrazol-4-yl)phenyl)imidazo[1,2-a]pyrazin-8-yl)amino)-2-ethylbenzamido)methyl)piperidin-1-yl)methyl)azetidine-1-carboxylate | 794.6 | Intermediate B4; Intermediate C3 |

Intermediate E1 tert-Butyl 3-[[4-[[[4-[[3-(6-chloro-2-fluoro-3-pyridyl)imidazo[1,2-a]pyrazin-8-yl]amino]-2-ethyl-benzoyl]amino]methyl]-1-piperidyl]methyl]azetidine-1-carboxylate To a 25 mL microwave vial was added tert-butyl 3-((4-((2-ethyl-4-((3-iodoimidazo[1,2-a]pyrazin-8-yl)amino)benzamido)methyl)piperidin-1-yl)methyl)azetidine-1-carboxylate (100 mg, 148 μmol) and (6-chloro-2-fluoropyridin-3-yl)boronic acid (28.6 mg, 163 μmol), $PdCl_2$(DPPF)-$CH_2Cl_2$ adduct (21.7 mg, 29.7 μmol) and $Na_2CO_3$ (47.2 mg, 445 μmol) in Dioxane (10 mL)/Water (1 mL). The vial capped and heated at 100° C. for 2 h under $N_2$. The reaction was directly used to the next step. MS $[M+H]^+$: 677.5.

The following intermediates were prepared in analogy:

| Int. | Name | MS ESI $[M + H]^+$ | Starting Material |
|---|---|---|---|
| Intermediate E2 | tert-butyl 3-[[4-[[[4-[[3-(6-chloro-4-methyl-3-pyridyl)imidazo[1,2-a]pyrazin-8-yl]amino]-2-ethyl-benzoyl]amino]methyl]-1-piperidyl]methyl]azetidine-1-carboxylate | 673.5 | Intermediate C3; (6-chloro-4-methylpyridin-3-yl)boronic |
| Intermediate E3 | tert-butyl 3-[[4-[[[4-[[3-(6-chloro-5-fluoro-3-pyridyl)imidazo[1,2-a]pyrazin-8-yl]amino]-2-ethyl-benzoyl]amino]methyl]-1-piperidyl]methyl]azetidine-1-carboxylate | 677.6 | Intermediate C3; (6-chloro-5-fluoropyridin-3-yl)boronic acid |

Intermediate F1 tert-Butyl 3-[[4-[[[2-ethyl-4-[[3-[2-fluoro-6-(3-methyl-1H-pyrazol-4-yl)-3-pyridyl]imidazo[1,2-a]pyrazin-8-yl]amino]benzoyl]amino]methyl]-1-piperidyl]methyl]azetidine-1-carboxylate To a 25 mL microwave vial, tert-butyl 3-((4-((4-((3-(6-chloro-2-fluoropyridin-3-yl)imidazo[1,2-a]pyrazin-8-yl)amino)-2-ethylbenzamido)methyl)piperidin-1-yl)methyl)azetidine-1-carboxylate (101 mg, 149 μmol), 3-methyl-4-(4,4,5,5-tetramethyl-1,3,2-dioxaborolan-2-yl)-1H-pyrazole (46.5 mg, 224 μmol), 1,1'-bis(di-tert-butylphosphino)ferrocene palladium dichloride (9.72 mg, 14.9 μmol) and $Na_2CO_3$ (31.6 mg, 298 μmol) was added with Dioxane (10 mL)/Water (1 mL). The microwave vial capped and heated at 110° C. for 2 h under $N_2$. The reaction mixture filtered through glass fiber paper. The crude filtrate was concentrated in vacuum. The crude material purified by flash chromatography (silica gel, 20 g, 0% to 20% MeOH in DCM) to afford tert-butyl 3-[[4-[[[2-ethyl-4-[[3-[2-fluoro-6-(3-methyl-1H-pyrazol-4-yl)-3-pyridyl]imidazo[1,2-a]pyrazin-8-yl]amino]benzoyl]amino]methyl]-1-piperidyl]methyl]azetidine-1-carboxylate (60 mg, 83 μmol, 55.7% yield). MS$[M+H]^+$: 723.5.

The following intermediates were prepared in analogy:

| Int. | Name | MS ESI $[M + H]^+$ | Starting Material |
|---|---|---|---|
| Intermediate F2 | tert-butyl 3-[[4-[[[2-ethyl-4-[[3-[4-methyl-6-(3-methyl-1H-pyrazol-4-yl)-3-pyridyl]imidazo[1,2-a]pyrazin-8-yl]amino]benzoyl]amino]methyl]-1-piperidyl]methyl]azetidine-1-carboxylate | 719.7 | Intermediate E2; 3-methyl-4-(4,4,5,5-tetramethyl-1,3,2-dioxaborolan-2-yl)-1H-pyrazole |

-continued

| Int. | Name | MS ESI [M + H]$^+$ | Starting Material |
|---|---|---|---|
| Intermediate F3 | tert-butyl 3-[[4-[[[2-ethyl-4-[[3-[5-fluoro-6-(3-methyl-1H-pyrazol-4-yl)-3-pyridyl]imidazo[1,2-a]pyrazin-8-yl]amino]benzoyl]amino]methyl]-1-piperidyl]methyl]azetidine-1-carboxylate | 723.7 | Intermediate E3; 3-methyl-4-(4,4,5,5-tetramethyl-1,3,2-dioxaborolan-2-yl)-1H-pyrazole |
| Intermediate F4 | tert-butyl 3-[[4-[[[4-[[3-[6-(3,5-dimethyl-1H-pyrazol-4-yl)-2-fluoro-3-pyridyl]imidazo[1,2-a]pyrazin-8-yl]amino]-2-ethyl-benzoyl]amino]methyl]-1-piperidyl]methyl]azetidine-1-carboxylate | 737.6 | Intermediate E1; 3,5-dimethyl-4-(4,4,5,5-tetramethyl-1,3,2-dioxaborolan-2-yl)-1H-pyrazole |

Intermediate G1

4-[[3-[2,3-Difluoro-4-[1-(2-methoxyethyl)-3-methyl-pyrazol-4-yl]phenyl]imidazo[1,2-a]pyrazin-8-yl]amino]-2-ethyl-N-[(1-methyl-4-piperidyl)methyl]benzamide

Step 1: 4-[[3-[2,3-difluoro-4-[l-(2-methoxyethyl)-3-methyl-pyrazol-4-yl]phenyl]imidazo[1,2-a]pyrazin-8-yl]amino]-2-ethyl-N-(4-piperidylmethyl)benzamide In a 50 mL round-bottomed flask, tert-butyl 4-((4-((3-(2,3-difluoro-4-(1-(2-methoxyethyl)-3-methyl-1H-pyrazol-4-yl)phenyl)imidazo[1,2-a]pyrazin-8-yl)amino)-2-ethylbenzamido)methyl)piperidine-1-carboxylate (275 mg, 377 μmol) was combined with THE (2 mL) to give a light brown solution. HCl (1.89 mL, 22.6 mmol) added. The reaction stirred at room temperature for 20 min. The crude reaction mixture was concentrated in vacuum, the crude product was directly used to the next step to afford 4-[[3-[2,3-difluoro-4-[1-(2-methoxyethyl)-3-methyl-pyrazol-4-yl]phenyl]imidazo[1,2-a]pyrazin-8-yl]amino]-2-ethyl-N-(4-piperidylmethyl)benzamide (237 mg, 377 μmol, 99.9% yield). MS [M+H]$^+$: 629.5.

Step 2: 4-[[3-[2,3-difluoro-4-[1-(2-methoxyethyl)-3-methyl-pyrazol-4-yl]phenyl]-imidazo[1,2-a]pyrazin-8-yl]amino]-2-ethyl-N-[(1-methyl-4-piperidyl)methyl]benzamide In a 50 mL round-bottomed flask, 4-((3-(2,3-difluoro-4-(1-(2-methoxyethyl)-3-methyl-1H-pyrazol-4-yl)phenyl)imidazo[1,2-a]pyrazin-8-yl)amino)-2-ethyl-N-(piperidin-4-ylmethyl)benzamide (237 mg, 377 μmol), formaldehyde (153 mg, 1.88 mmol) and $NaBH_3CN$ (118 mg, 1.88 mmol) were combined with MeOH (6 mL) to give a light brown solution. The reaction mixture heated to 50° C. and stirred for 20 min. The crude reaction mixture was concentrated in vacuum. The reaction mixture was poured into 25 mL sat $NaHCO_3$ and extracted with EtOAc (25 mL×3). The organic layers were combined, washed with sat NaCl (25 mL). Dried over $Na_2SO_4$ and concentrated in vacuum to afford 4-((3-(2,3-difluoro-4-(1-(2-methoxyethyl)-3-methyl-1H-pyrazol-4-yl)phenyl)imidazo[1,2-a]pyrazin-8-yl)amino)-2-ethyl-N-((1-methylpiperidin-4-yl)methyl)benzamide (242 mg, 377 μmol, 99.9% yield) MS[M+H]$^+$: 643.4.

The following intermediates were prepared in analogy:

| Int. | Name | MS ESI [M + H]$^+$ | Starting Material |
|---|---|---|---|
| Intermediate G2 | 4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-N-[(1-methyl-4-piperidyl)methyl]benzamide | 657.3 | Intermediate D7 |

Example A1

N-[[1-(Azetidin-3-ylmethyl)-4-piperidyl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formic acid

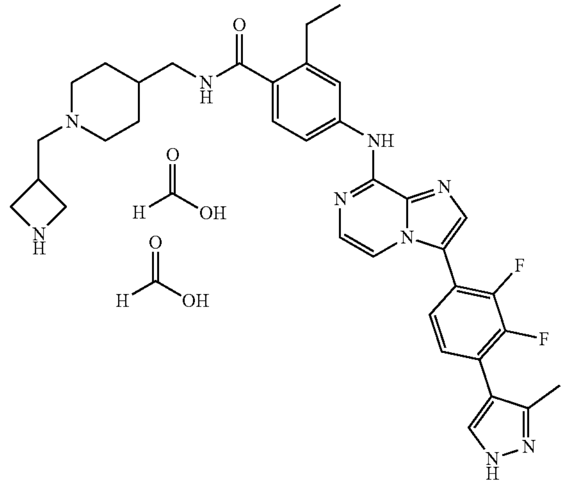

In a 100 mL round-bottomed flask, tert-butyl 3-((4-((4-((3-(2,3-difluoro-4-(3-methyl-1-((2-(trimethylsilyl)ethoxy)methyl)-1H-pyrazol-4-yl)phenyl)imidazo[1,2-a]pyrazin-8-yl)amino)-2-ethylbenzamido)methyl)piperidin-1-yl)methyl)azetidine-1-carboxylate (39 mg, 44.8 μmol) was combined with DCM (3 mL) to give a light brown solution. 2,2,2-trifluoroacetic acid (1.02 g, 8.96 mmol) was added. The reaction stirred at room temperature for 1 h. The crude reaction mixture was concentrated in vacuum. The crude material was purified by preparative HPLC, to obtain N-[[1-(azetidin-3-ylmethyl)-4-piperidyl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formic acid (9 mg, 10.2 μmol, 22.7% yield). MS [M+H]+. 640.2.

Example A2

N-[[1-(Azetidin-3-ylmethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formic acid; formate

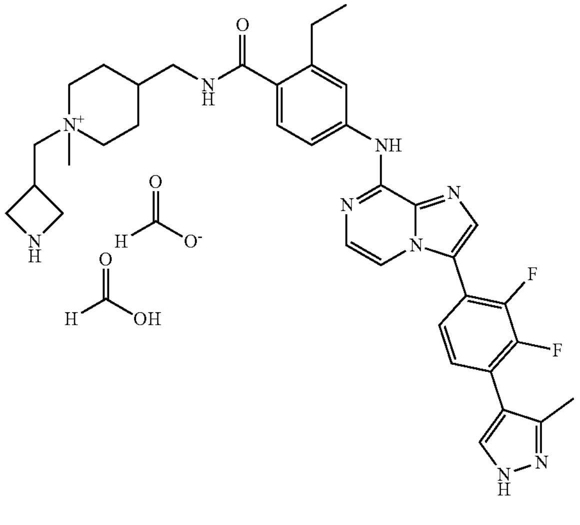

Step 1: tert-butyl 3-[[4-[[[4-[[3-[2,3-difluoro-4-[3-methyl-1-(2-trimethylsilylethoxymethyl) pyrazol-4-yl]phenyl]imidazo[1,2-a]pyrazin-8-yl]amino]-2-ethyl-benzoyl]amino]methyl]-1-methyl-piperidin-1-ium-1-yl]methyl]azetidine-1-carboxylate; iodide In a 50 mL round-bottomed flask, tert-butyl 3-((4-((4-((3-(2,3-difluoro-4-(3-methyl-1-((2-(trimethylsilyl)ethoxy)methyl)-1H-pyrazol-4-yl)phenyl)imidazo[1,2-a]pyrazin-8-yl)amino)-2-ethylbenzamido)methyl)piperidin-1-yl)methyl)azetidine-1-carboxylate (29 mg, 33.3 μmol) and MeI (23.7 mg, 167 μmol) and DIPEA (21.5 mg, 167 μmol) were combined with MeCN (3 mL) to give a light brown solution. The reaction stirred at room temperature for 2 h. The crude reaction mixture was concentrated in vacuum to afford tert-butyl 3-[[4-[[[4-[[3-[2,3-difluoro-4-[3-methyl-1-(2-trimethylsilylethoxymethyl)pyrazol-4-yl]phenyl]imidazo[1,2-a]pyrazin-8-yl]amino]-2-ethyl-benzoyl]amino]methyl]-1-methyl-piperidin-1-ium-1-yl]methyl]azetidine-1-carboxylate; iodide (29.5 mg, 33.3 μmol, 100% yield). MS $[M+H]^+$: 884.9.

Step 2: N-[[1-(azetidin-3-ylmethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formic acid; formate In a 50 mL round-bottomed flask, 1-((1-(tert-butoxycarbonyl)azetidin-3-yl)methyl)-4-((4-((3-(2,3-difluoro-4-(3-methyl-1-((2-(trimethylsilyl)ethoxy)methyl)-1H-pyrazol-4-yl)phenyl)imidazo[1,2-a]pyrazin-8-yl)amino)-2-ethylbenzamido)methyl)-1-methylpiperidin-1-ium (29.5 mg, 33.3 μmol) and HCl (in water) (1.11 mL, 13.3 mmol) were combined with THE (2 mL) to give a light brown solution. HCl (in water) (1.11 mL, 13.3 mmol) added. The reaction stirred at room temperature for 1 h. The crude reaction mixture was concentrated in vacuum. The crude material purified by preparative HPLC to afford N-[[1-(azetidin-3-ylmethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formic acid; formate (9.4 mg, 12.4 μmol, 37.1% yield). MS: 654.8.

The following compounds were prepared in analogy:

| Ex. | Name | Structure | MS ESI [M + H]+ | Starting Material |
|---|---|---|---|---|
| Example A3 | 2-[4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]-1-piperidyl]acetic acid | 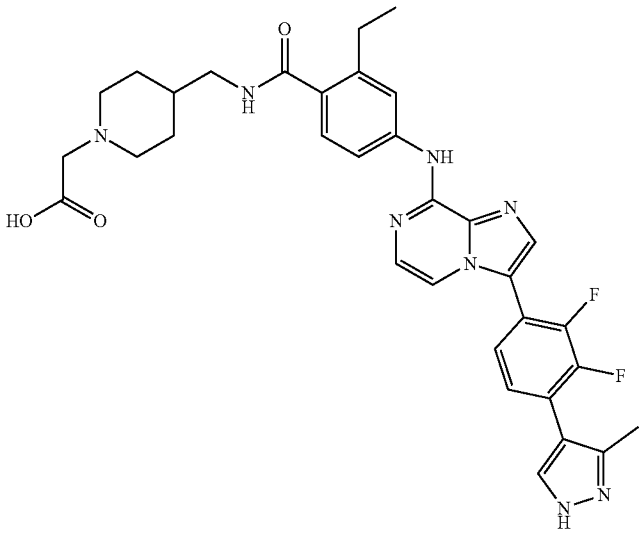 [SMILES: CCc1cc(Nc2nccn3c(-c4ccc(-c5c[nH]nc5C)c(F)c4F)cnc23)ccc1C(=O)NCC1CCN(CC(=O)O)CC1] | 674.7 | Intermediate D4 |
| Example A4 | 2-[4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]-1-methyl-piperidin-1-ium-1-yl]acetic acid; formate | 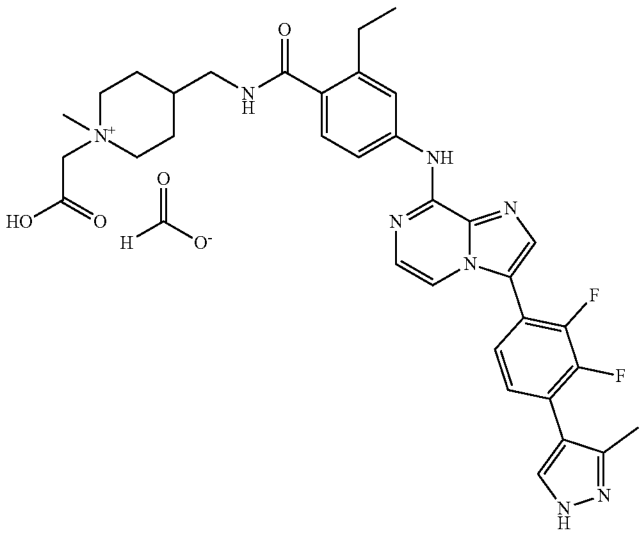 | 643.5 | Intermediate D4 |
| Example A5 | 2-[1-(azetidin-3-ylmethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid; formic acid; formate | 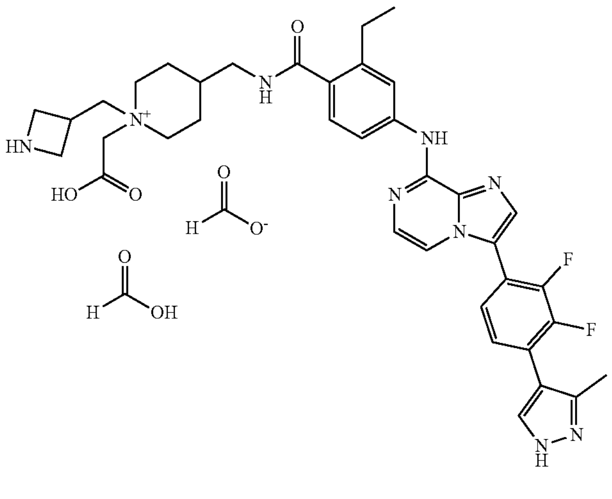 | 698.8 | Intermediate D3; tert-butyl 2-bromoacetate |

-continued
| Ex. | Name | Structure | MS ESI $[M + H]^+$ | Starting Material |
|---|---|---|---|---|
| Example A6 | 4-[[3-[2,3-difluoro-4-(3-methyl-1H-pyrazol-4-yl)phenyl]imidazo[1,2-a]pyrazin-8-yl]amino]-2-ethyl-N-(4-piperidylmethyl) benzamide; formic acid | 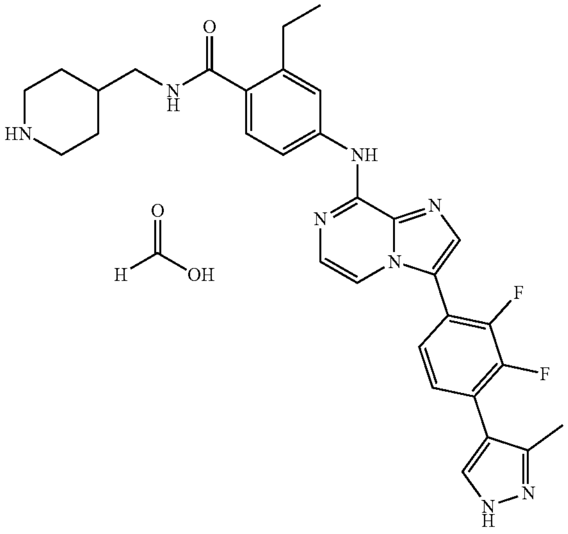 [SMILES: CCc1cc(Nc2nccn3c(-c4ccc(-c5c[nH]nc5C)c(F)c4F)cnc23)ccc1C(=O)NCC1CCNCC1 ; O=CO] | 571.5 | Intermediate D5 |
| Example A7 | N-[[1-(2-amino-2-oxo-ethyl)-1-methyl-piperidin-1-ium-4-yl]methyl]-4-[[3-[2,3-difluoro-4-(3-methyl-1H-pyrazol-4-yl)phenyl]imidazo[1,2-a]pyrazin-8-yl]amino]-2-ethyl-benzamide; formate | 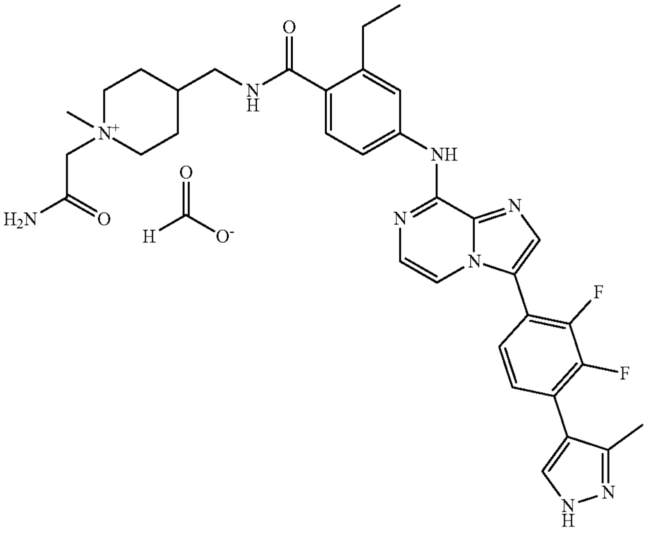 | 642.5 | Intermediate D2 |

-continued

| Ex. | Name | Structure | MS ESI [M + H]+ | Starting Material |
|---|---|---|---|---|
| Example A8 | 2-[1-(2-amino-2-oxo-ethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid; formate | 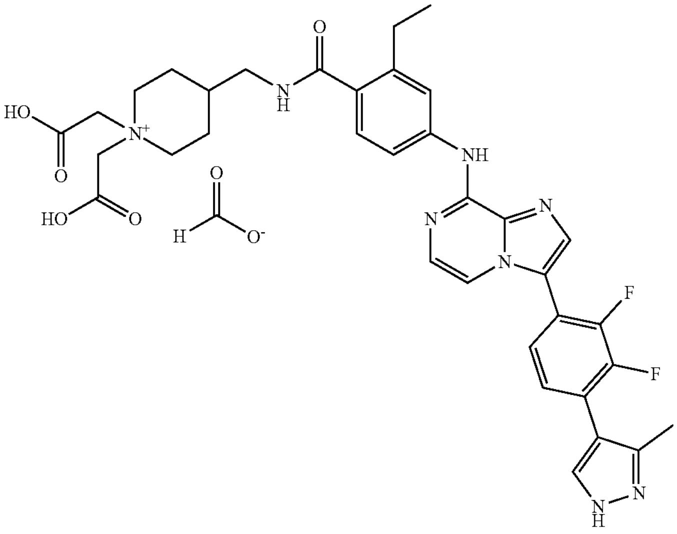 | 686.5 | Intermediate D4 |
| Example A9 | 2-[1-(carboxymethyl)-4-[[[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid; formate | 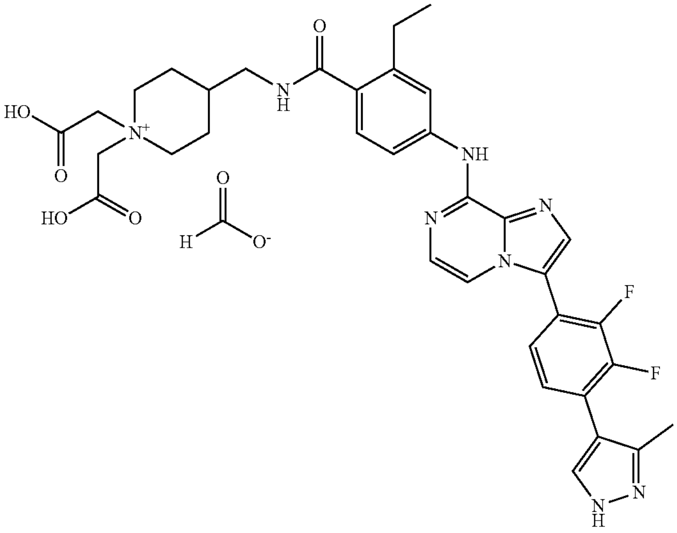 | 687.4 | Intermediate D4; tert-butyl 2-bromoacetate |

-continued

| Ex. | Name | Structure | MS ESI [M + H]+ | Starting Material |
| --- | --- | --- | --- | --- |
| Example A10 | N-[[1-(azetidin-3-ylmethyl)-4-piperidyl]methyl]-2-ethyl-4-[[3-[2-fluoro-6-(3-methyl-1H-pyrazol-4-yl)-3-pyridyl]imidazo[1,2-a]pyrazin-8-yl]amino]benzamide; formic acid | 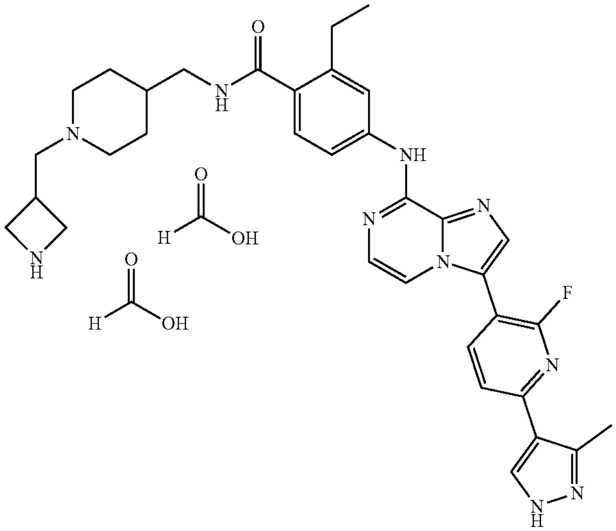 | 623.5 | Intermediate F1 |
| Example A11 | N-[[1-(azetidin-3-ylmethyl)-4-piperidyl]methyl]-4-[[3-[6-(3,5-dimethyl-1H-pyrazol-4-yl)-2-fluoro-3-pyridyl]imidazo[1,2-a]pyrazin-8-yl]amino]-2-ethyl-benzamide; formic acid | 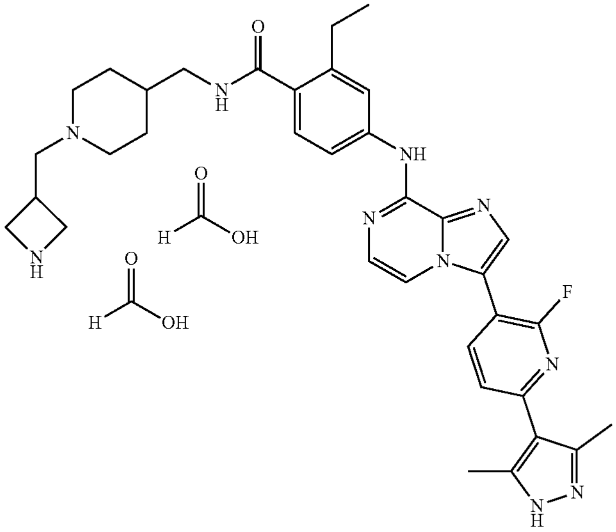 | 637.6 | Intermediate F4 |

-continued

| Ex. | Name | Structure | MS ESI $[M + H]^+$ | Starting Material |
| --- | --- | --- | --- | --- |
| Example A12 | N-[[1-(azetidin-3-ylmethyl)-4-piperidyl]methyl]-4-[[3-[2,3-difluoro-4-[3-(trifluoromethyl)-1H-pyrazol-4-yl]phenyl]imidazo[1,2-a]pyrazin-8-yl]amino]-2-ethyl-benzamide; formic acid | 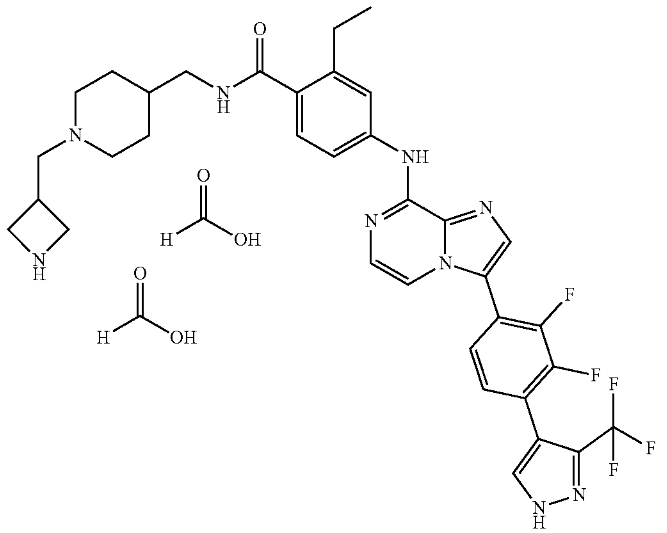 | 694.5 | Intermediate D9 |

Example B1

N-[[1-(Azetidin-3-ylmethyl)-1-methyl-piperidin-1-ium-4-yl]methyl]-2-ethyl-4-[[3-[2-fluoro-6-(3-methyl-1H-pyrazol-4-yl)-3-pyridyl]imidazo[1,2-a]pyrazin-8-yl]amino]benzamide; formic acid; formate

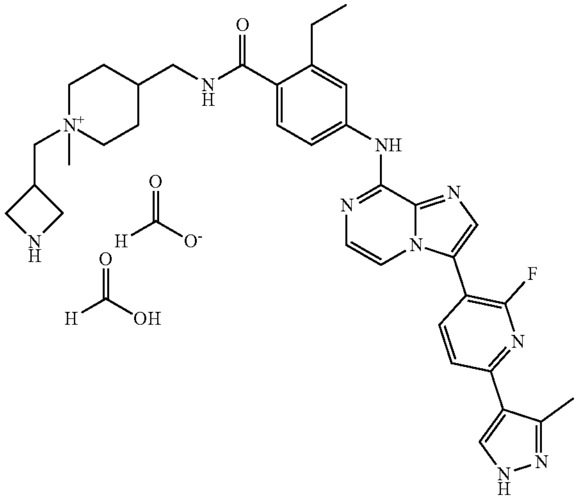

Step 1: tert-butyl 4-(5-(8-((4-(((1-((1-(tert-butoxycarbonyl)azetidin-3-yl)methyl)piperidin-4-yl)methyl)carbamoyl)-3-ethylphenyl)amino)imidazo[1,2-a]pyrazin-3-yl)-6-fluoropyridin-2-yl)-3-methyl-1H-pyrazole-1-carboxylate In a 50 mL round-bottomed flask, $Boc_2O$ (24.2 mg, 111 μmol), tert-butyl 3-((4-((2-ethyl-4-((3-(2-fluoro-6-(3-methyl-1H-pyrazol-4-yl)pyridin-3-yl)imidazo[1,2-a]pyrazin-8-yl)amino)benzamido)methyl)piperidin-1-yl)methyl)azetidine-1-carboxylate (40 mg, 55.3 μmol,), DMAP (2.03 mg, 16.6 μmol) and DIPEA (21.5 mg, 166 μmol) were combined with THF (3 mL) to give a light brown solution. The reaction mixture stirred at 50° C. for 2 hs. The crude reaction mixture was concentrated in vacuum to afford tert-butyl 4-(5-(8-((4-(((1-((1-(tert-butoxycarbonyl)azetidin-3-yl)methyl)piperidin-4-yl)methyl)carbamoyl)-3-ethylphenyl)amino)imidazo[1,2-a]pyrazin-3-yl)-6-fluoropyridin-2-yl)-3-methyl-1H-pyrazole-1-carboxylate (45.5 mg, 55.3 μmol, 99.9% yield). MS: 823.7.

Step 2: tert-butyl 3-[[4-[[[4-[[3-[6-(1,3-dimethylpyrazol-4-yl)-2-fluoro-3-pyridyl]imidazo[1,2-a]pyrazin-8-yl]amino]-2-ethyl-benzoyl]amino]methyl]-1-methyl-piperidin-1-ium-1-yl]methyl]azetidine-1-carboxylate; iodide In a 50 mL round-bottomed flask, tert-butyl 4-(5-(8-((4-(((1-((1-(tert-butoxycarbonyl)azetidin-3-yl)methyl)piperidin-4-yl)methyl)carbamoyl)-3-ethylphenyl)amino)imidazo[1,2-a]pyrazin-3-yl)-6-fluoropyridin-2-yl)-3-methyl-1H-pyrazole-1-carboxylate (45 mg, 54.7 μmol), MeI (38.8 mg, 17.1 μl, 273 μmol) and DIPEA (35.3 mg, 47.8 μl, 273 μmol) were combined with MeCN (5 mL) to give a light red solution. The reaction mixture heated to 45° C. and stirred for 1 h. The crude reaction mixture concentrated in vacuum. the crude product was directly used to the next step, to afford tert-butyl 3-[[4-[[[4-[[3-[6-(1,3-dimethylpyrazol-4-yl)-2-fluoro-3-pyridyl]imidazo[1,2-a]pyrazin-8-yl]amino]-2-ethyl-benzoyl]amino]methyl]-1-methyl-piperidin-1-ium-1-yl]methyl]azetidine-1-carboxylate; iodide (45.8 mg, 54.7 μmol, 100% yield). MS: 837.7.

Step 3: N-[[1-(azetidin-3-ylmethyl)-1-methyl-piperidin-1-ium-4-yl]methyl]-2-ethyl-4-[[3-[2-fluoro-6-(3-methyl-1H-pyrazol-4-yl)-3-pyridyl]imidazo[1,2-a]pyrazin-8-yl]amino]benzamide; formic acid; formate In a 50 mL round-bottomed flask, 4-((4-((3-(6-(1-(tert-butoxycarbonyl)-3-methyl-1H-pyrazol-4-yl)-2-fluoropyridin-3-yl)imidazo[1,2-a]pyrazin-8-yl)amino)-2-ethylbenzamido)methyl)-1-((1-(tert-butoxycarbonyl)azetidin-3-yl)methyl)-1-methylpiperidin-1-ium (45 mg, 53.7 μmol) was combined with THE (2 mL) to give a light red solution. HCl (in water) (1.34 mL, 16.1 mmol) was added. The reaction stirred at room temperature for 1 h. The crude reaction mixture was concentrated in vacuum. The crude material was purified by preparative HPLC to afford N-[[1-(azetidin-3-ylmethyl)-1-methyl-piperidin-1-ium-4-yl]methyl]-2-ethyl-4-[[3-[2-fluoro-6-(3-methyl-1H-pyrazol-4-yl)-3-pyridyl]imidazo[1,2-a]pyrazin-8-yl]amino]benzamide; formic acid; formate (6.6 mg, 8.87 μmol, 16.5% yield). MS: 637.

The following compounds were prepared in analogy:

| Int. | Name | Structure | MS ESI | Starting Material |
|---|---|---|---|---|
| Example B2 | N-[[1-(azetidin-3-ylmethyl)-1-methyl-piperidin-1-ium-4-yl]methyl]-2-ethyl-4-[[3-[4-methyl-6-(3-methyl-1H-pyrazol-4-yl)-3-pyridyl]imidazo[1,2-a]pyrazin-8-yl]amino]benzamide; formic acid; formate | 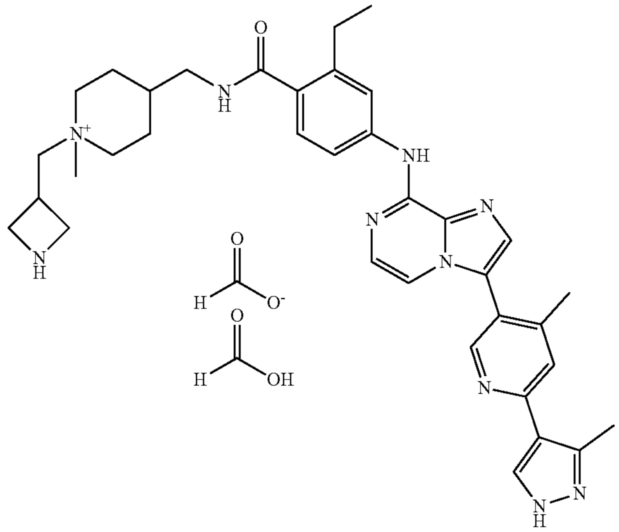 | 633.6 | Intermediate F2 |
| Example B3 | N-[[1-(azetidin-3-ylmethyl)-1-methyl-piperidin-1-ium-4-yl]methyl]-2-ethyl-4-[[3-[5-fluoro-6-(3-methyl-1H-pyrazol-4-yl)-3-pyridyl]imidazo[1,2-a]pyrazin-8-yl]amino]benzamide; formic acid; formate | 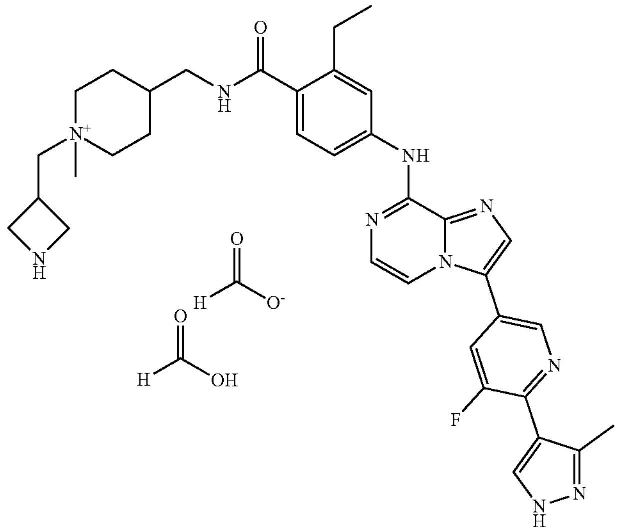 | 637.5 | Intermediate F3 |

-continued

| Int. | Name | Structure | MS ESI | Starting Material |
| --- | --- | --- | --- | --- |
| Example B4 | N-[[1-(azetidin-3-ylmethyl)-1-methyl-piperidin-1-ium-4-yl]methyl]-4-[[3-[6-(3,5-dimethyl-1H-pyrazol-4-yl)-2-fluoro-3-pyridyl]imidazo[1,2-a]pyrazin-8-yl]amino]-2-ethyl-benzamide; formic acid; formate | 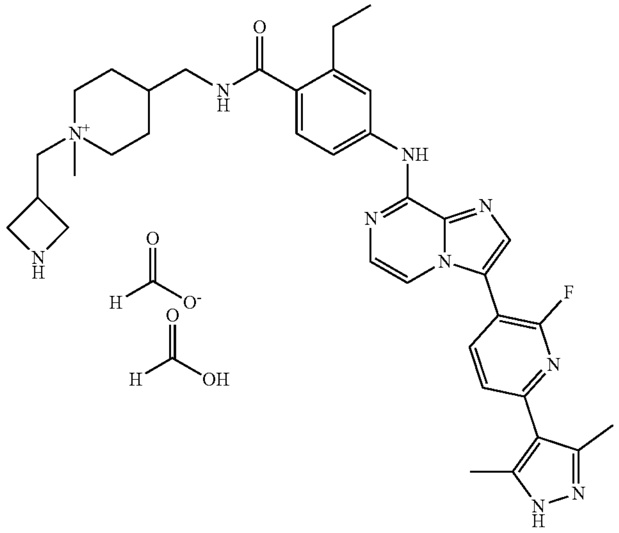 | 651.5 | Intermediate F4 |
| Example B5 | N-[[1-(azetidin-3-ylmethyl)-1-methyl-piperidin-1-ium-4-yl]methyl]-2-ethyl-4-[[3-[4-(3-methyl-1H-pyrazol-4-yl)phenyl]imidazo[1,2-a]pyrazin-8-yl]amino]benzamide; formic acid; formate | 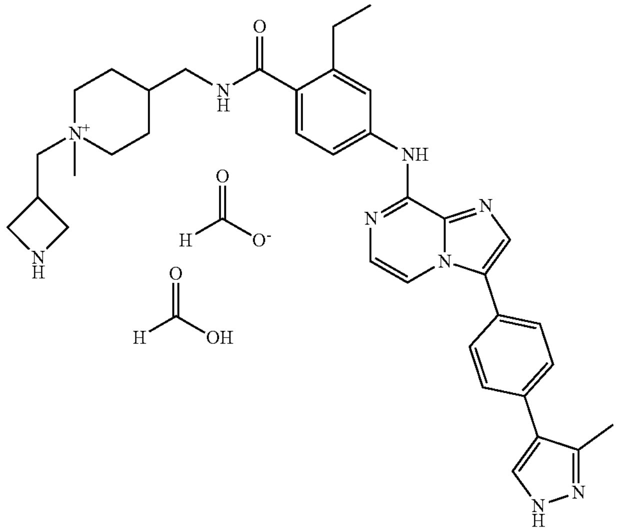 | 618.6 | Intermediate D8 |
| Example B6 | N-[[1-(azetidin-3-ylmethyl)-1-methyl-piperidin-1-ium-4-yl]methyl]-4-[[3-[2,3-difluoro-4-[3-(trifluoromethyl)-1H-pyrazol-4-yl]phenyl]imidazo[1,2-a]pyrazin-8-yl]amino]-2-ethyl-benzamide; formic acid; formate | 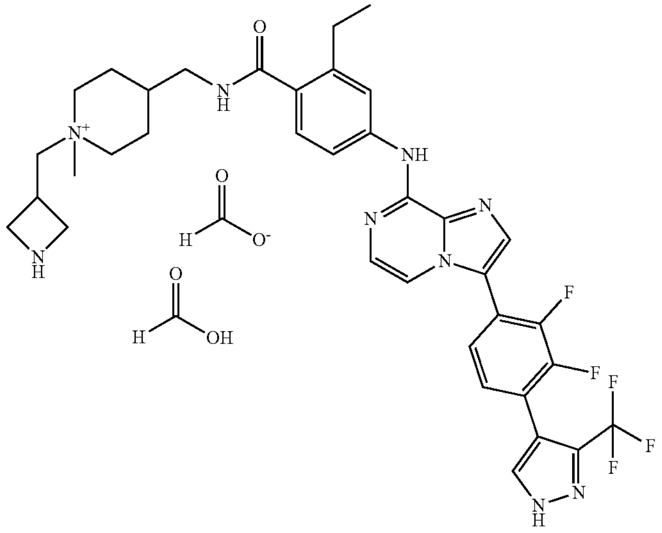 | 708.5 | Intermediate D9 |

Example C1

4-[[3-[2,3-Difluoro-4-[1-(2-methoxyethyl)-3-methyl-pyrazol-4-yl]phenyl]imidazo[1,2-a]pyrazin-8-yl]amino]-N-[(1,1-dimethylpiperidin-1-ium-4-yl)methyl]-2-ethyl-benzamide; formate

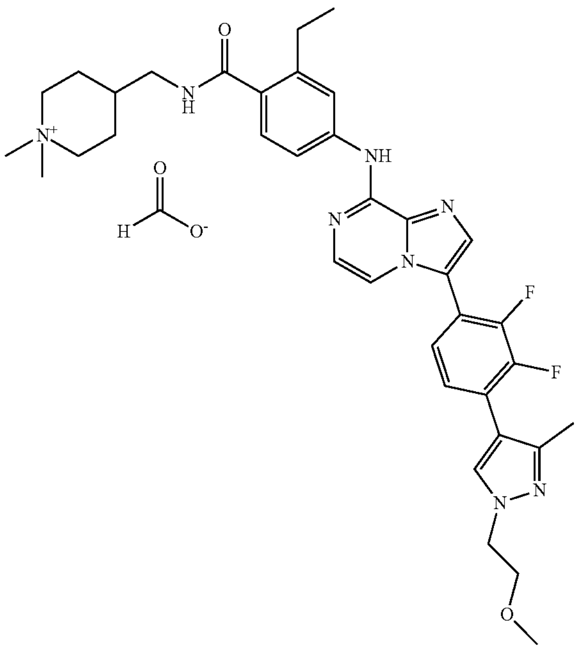

In a 50 mL round-bottomed flask, 4-((3-(2,3-difluoro-4-(1-(2-methoxyethyl)-3-methyl-1H-pyrazol-4-yl)phenyl)imidazo[1,2-a]pyrazin-8-yl)amino)-2-ethyl-N-((1-methylpiperidin-4-yl)methyl)benzamide (60 mg, 93.3 μmol), MeI (66.2 mg, 29.2 μl, 467 μmol) and DIPEA (60.3 mg, 81.5 μl, 467 μmol) were combined with MeCN (5 mL) to give a light brown solution. The reaction stirred at room temperature for 15 h. The crude reaction mixture was concentrated in vacuum. The crude material was purified by preparative HPLC to afford 4-[[3-[2,3-difluoro-4-[1-(2-methoxyethyl)-3-methyl-pyrazol-4-yl]phenyl]imidazo[1,2-a]pyrazin-8-yl]amino]-N-[(1,1-dimethylpiperidin-1-ium-4-yl)methyl]-2-ethyl-benzamide; formate (10.6 mg, 14.8 μmol, 15.8% yield). MS: 657.5.

The following compounds were prepared in analogy:

| Int. | Name | Structure | MS ESI [M + H]$^+$ | Starting Material |
|---|---|---|---|---|
| Example C2 | N-[[1-(2-amino-2-oxo-ethyl)-1-methyl -piperidin-1-ium-4-yl]methyl]-4-[[3-[2,3-difluoro-4-[1-(2-methoxyethyl)-3-methyl-pyrazol-4-yl]phenyl]imidazo[1,2-a]pyrazin-8-yl]amino]-2-ethyl-benzamide; formate | 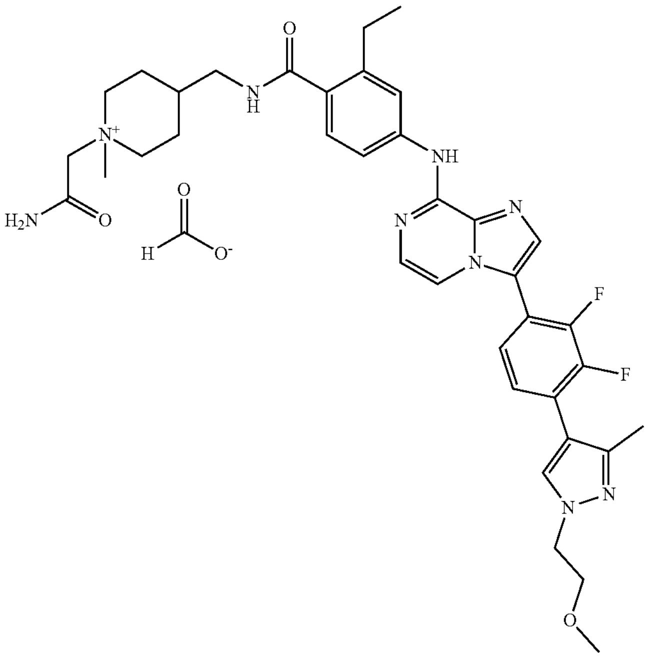 | 700.5 | Intermediate G1; 2-iodoacetamide |

-continued

| Int. | Name | Structure | MS ESI [M + H]$^+$ | Starting Material |
|---|---|---|---|---|
| Example C3 | 4-[[3-[2,3-difluoro-4-[1-(2-methoxyethyl)-3-methyl-pyrazol-4-yl]phenyl]imidazo[1,2-a]pyrazin-8-yl]amino]-2-ethyl-N-[[1-(2-hydroxyethyl)-1-methyl-piperidin-1-ium-4-yl]methyl]benzamide; formate | 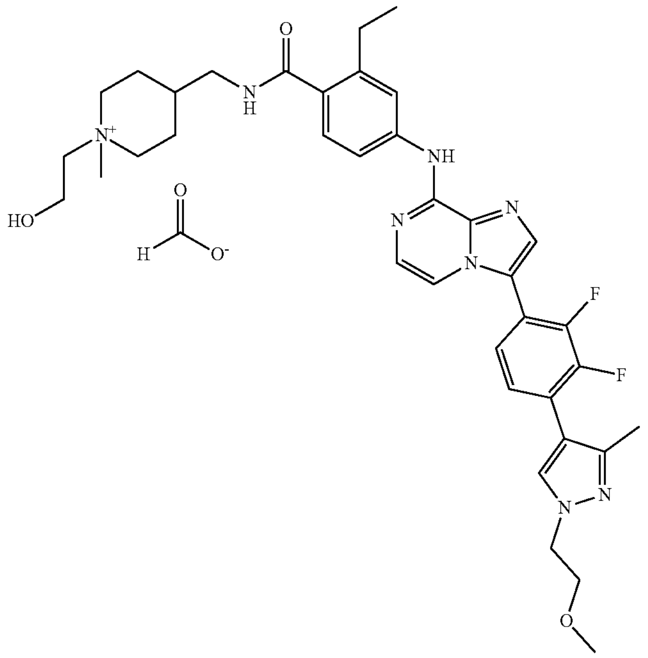 | 687.5 | Intermediate G1; 2-bromoethanol |
| Example C4 | N-[[1-(azetidin-3-ylmethyl)-1-methyl-piperidin-1-ium-4-yl]methyl]-4-[[3-[2,3-difluoro-4-[1-(2-methoxyethyl)-3-methyl-pyrazol-4-yl]phenyl]imidazo[1,2-a]pyrazin-8-yl]amino]-2-ethyl-benzamide; formic acid; formate | 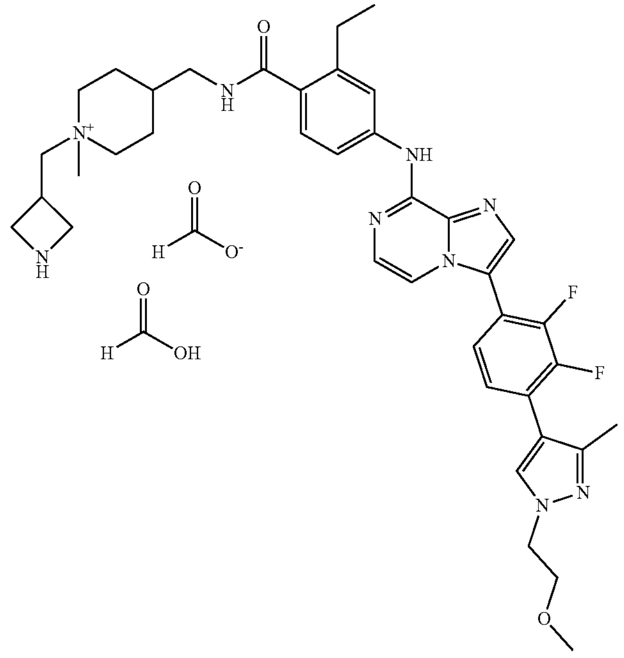 | 712.5 | Intermediate G1; tert-butyl 3-(iodomethyl) azetidine-1-carboxylate |

-continued

| Int. | Name | Structure | MS ESI $[M + H]^+$ | Starting Material |
|---|---|---|---|---|
| Example C5 | N-[[1-(2-amino-2-oxo-ethyl)-1-methyl-piperidin-1-ium-4-yl]methyl]-4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-benzamide; formate | 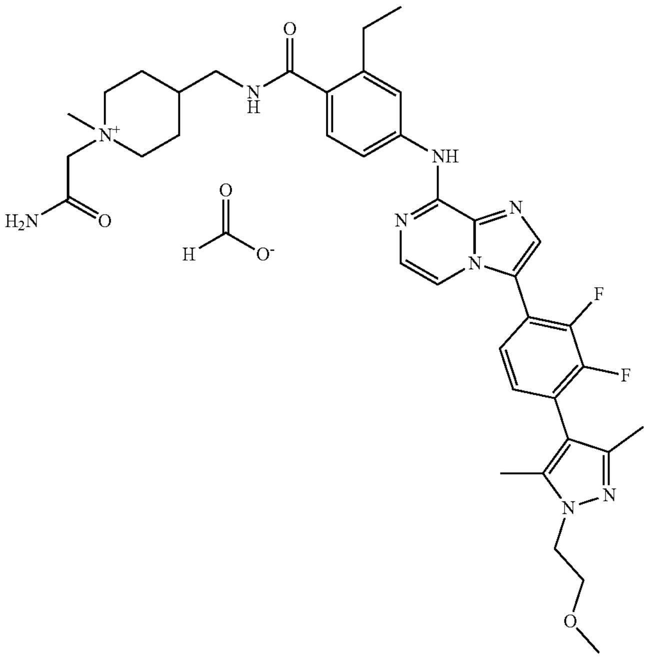 | 712.4 | Intermediate G2; 2-iodoacetamide |
| Example C6 | 4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-N-[[1-(2-hydroxyethyl)-1-methyl-piperidin-1-ium-4-yl]methyl]benzamide; formate | 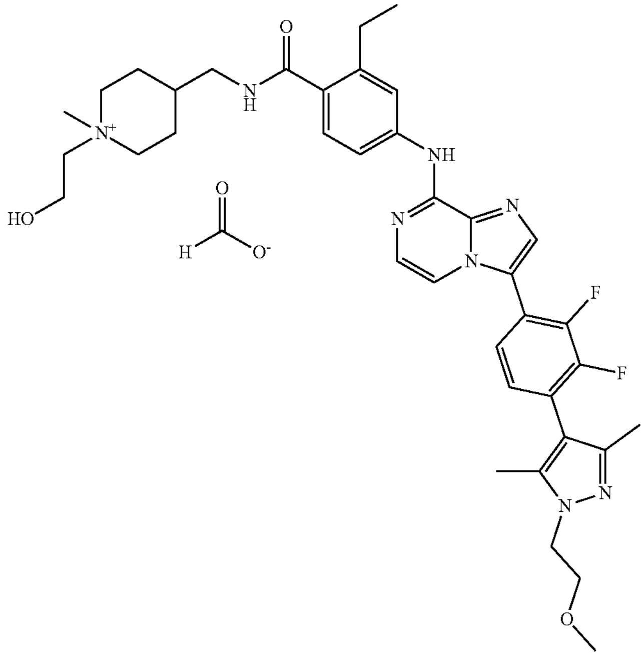 | 701.5 | Intermediate G2; 2-iodoethan-1-ol |

-continued

| Int. | Name | Structure | MS ESI $[M + H]^+$ | Starting Material |
|---|---|---|---|---|
| Example C7 | N-[[1-(azetidin-3-ylmethyl)-1-methyl-piperidin-1-ium-4-yl]methyl]-4-[[3-[2,3-difluoro-4-[1-(2-methoxyethyl)-3,5-dimethyl-pyrazol-4-yl]phenyl]imidazo[1,2-a]pyrazin-8-yl]amino]-2-ethyl-benzamide; formic acid; formate | 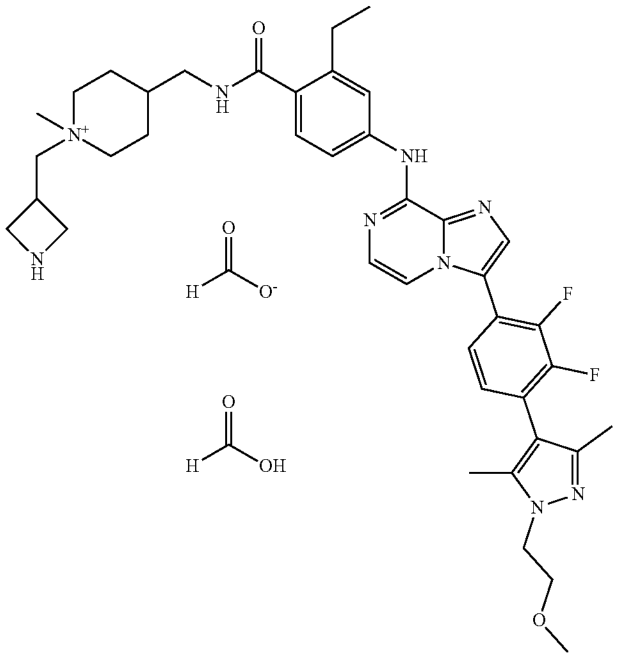 | 712.4 | Intermediate G2; tert-butyl 3-(iodomethyl) azetidine-1-carboxylate |

Example D1

N-[[1-(2-Amino-2-oxo-ethyl)-1-methyl-piperidin-1-ium-4-yl]methyl]-4-[[3-[4-[1-(cyanomethyl)-3-methyl-pyrazol-4-yl]-2,3-difluoro-phenyl]imidazo[1,2-a]pyrazin-8-yl]amino]-2-ethyl-benzamide; formate

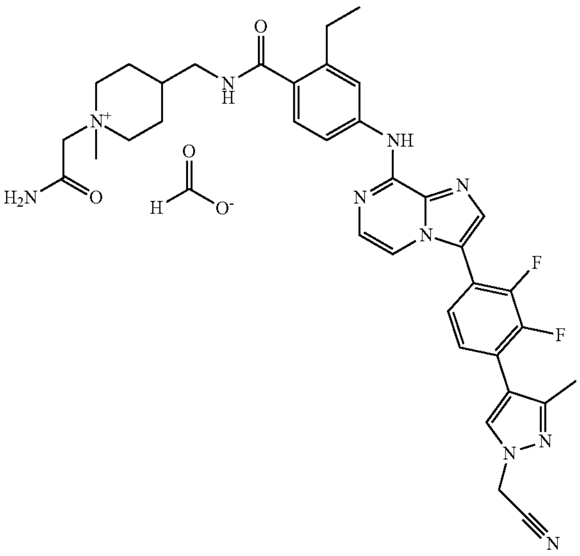

Step 1: N-((1-(2-amino-2-oxoethyl)piperidin-4-yl)methyl)-4-((3-(2,3-difluoro-4-(3-methyl-1H-pyrazol-4-yl)phenyl)imidazo[1,2-a]pyrazin-8-yl)amino)-2-ethylbenzamide In a 50 mL round-bottomed flask, N-((1-(2-amino-2-oxoethyl)piperidin-4-yl)methyl)-4-((3-(2,3-difluoro-4-(3-methyl-1-((2-(trimethylsilyl)ethoxy)methyl)-1H-pyrazol-4-yl)phenyl)imidazo[1,2-a]pyrazin-8-yl)amino)-2-ethylbenzamide (14 mg, 18.5 μmol) and HCl (462 μl, 5.54 mmol) were combined with THF (2 mL) to give a light brown solution. The reaction mixture heated to 45° C. and stirred for 15 h. The crude reaction mixture was concentrated in vacuum to afford N-((1-(2-amino-2-oxoethyl)piperidin-4-yl)methyl)-4-((3-(2,3-difluoro-4-(3-methyl-1H-pyrazol-4-yl)phenyl)imidazo[1,2-a]pyrazin-8-yl)amino)-2-ethylbenzamide (11.6 mg, 18.5 μmol, 100% yield). MS$[M+H]^+$: 628.5.

Step 2: N-((1-(2-amino-2-oxoethyl)piperidin-4-yl)methyl)-4-((3-(4-(1-(cyanomethyl)-3-methyl-1H-pyrazol-4-yl)-2,3-difluorophenyl)imidazo[1,2-a]pyrazin-8-yl)amino)-2-ethylbenzamide In a 50 mL round-bottomed flask, N-((1-(2-amino-2-oxoethyl)piperidin-4-yl)methyl)-4-((3-(2,3-difluoro-4-(3-methyl-1H-pyrazol-4-yl)phenyl)imidazo[1,2-a]pyrazin-8-yl)amino)-2-ethylbenzamide (11.6 mg, 18.5 μmol), 3-bromoprop-1-yne (4.4 mg, 37 μmol) and DIPEA (7.17 mg, 9.68 μl, 55.4 μmol) were combined with DCM (2 mL) to give a light brown solution. The reaction stirred at room temperature for 1 h. The crude reaction mixture was concentrated in vacuum to afford N-((1-(2-amino-2-oxoethyl)piperidin-4-yl)methyl)-4-((3-(4-(1-(cyanomethyl)-3-methyl-1H-pyrazol-4-yl)-2,3-difluorophenyl)imidazo[1,2- a]pyrazin-8-yl)amino)-2-ethylbenzamide (12.3 mg, 18.4 μmol, 99.8% yield). MS[M+H]$^+$: 667.8

Step 3: N-[[1-(2-amino-2-oxo-ethyl)-1-methyl-piperidin-1-ium-4-yl]methyl]-4-[[3-[4-[1-(cyanomethyl)-3-methyl-pyrazol-4-yl]-2,3-difluoro-phenyl] imidazo[1,2-a]pyrazin-8-yl]amino]-2-ethyl-benzamide; formate In a 50 mL round-bottomed flask, N-((1-(2-amino-2-oxoethyl)piperidin-4-yl)methyl)-4-((3-(4-(1-(cyanomethyl)-3-methyl-1H-pyrazol-4-yl)-2,3-difluorophenyl)imidazo[1,2-a]pyrazin-8-yl)amino)-2-ethylbenzamide (12.3 mg, 18.4 μmol), MeI (13.1 mg, 92.2 μmol) and DIPEA (11.9 mg, 16.1 μl, 92.2 μmol, Eq: 5) were combined with MeCN (3 mL) to give a light yellow solution. The reaction mixture heated to 45° C. and stirred for 15 h. The crude reaction mixture was concentrated in vacuum. The crude material purified by preparative HPLC to afford N-[[1-(2-amino-2-oxo-ethyl)-1-methyl-piperidin-1-ium-4-yl]methyl]-4-[[3-[4-[1-(cyanomethyl)-3-methyl-pyrazol-4-yl]-2,3-difluoro-phenyl]imidazo[1,2-a]pyrazin-8-yl]amino]-2-ethyl-benzamide; formate (6 mg, 7.84 μmol, 42.5% yield). MS: 681.5.

Assay Procedures

Antimicrobial Susceptibility Testing:

90% Growth Inhibitory Concentration (IC90) Determination

The in vitro antimicrobial activity of the compounds was determined according to the following procedure:

The assay used a 10-points Iso-Sensitest broth medium to measure quantitatively the in vitro activity of the compounds against *Acinetobacter baumannii* ATCC17961 and *Pseudomonas aeruginosa* ATCC27853.

Stock compounds in DMSO were serially twofold diluted (e.g. range from 50 to 0.097 μM final concentration) in 384 wells microtiter plates and inoculated with 49 μl the bacterial suspension in Iso-Sensitest medium to have a final cell concentration of ~$5\times10^{(5)}$ CFU/ml in a final volume/well of 50 ul/well. Microtiter plates were incubated at 35±2° C.

Bacterial cell growth was determined with the measurement of optical density at λ=600 nm each 20 minutes over a time course of 16 h. Growth inhibition was calculated during the logarithmic growth of the bacterial cells with determination of the concentration inhibiting 50% (IC50) and 90% (IC90) of the growth.

Table 1 provides the 90% growth inhibitory concentrations (IC90) in micromoles per liter of the compounds of present invention obtained against the strain *Acinetobacter baumannii* ATCC17961.

Particular compounds of the present invention exhibit an IC90 (*Acinetobacter baumannii* ATCC17961)<25 μmol/l.

More particular compounds of the present invention exhibit an IC90 (*Acinetobacter baumannii* ATCC17961)<5 μmol/l.

Most particular compounds of the present invention exhibit an IC90 (*Acinetobacter baumannii* ATCC17961)<1 μmol/l.

Table 2 provides the 90% growth inhibitory concentrations (IC90) in micromoles per liter of the compounds of present invention obtained against the strain *Pseudomonas aeruginosa* ATCC27853.

TABLE 1

| Example | ATCC 17961 IC90 [μM] |
|---|---|
| Example A1 | 0.047 |
| Example A2 | 0.05 |
| Example A3 | 0.34 |
| Example A4 | 0.31 |
| Example A5 | 0.15 |
| Example A12 | 0.28 |
| Example B1 | 1.10 |
| Example B4 | 0.43 |
| Example B5 | 0.10 |
| Example B6 | 0.16 |
| Example C1 | 0.27 |
| Example C2 | 0.29 |
| Example C3 | 0.43 |
| Example C4 | 0.46 |
| Example C5 | 0.68 |
| Example C6 | 0.44 |
| Example C7 | 0.32 |

TABLE 2

| Example | ATCC 27853 IC90 [μM] |
|---|---|
| Example A1 | 0.16 |
| Example A2 | 0.098 |
| Example A3 | 1.8 |
| Example A4 | 1.2 |
| Example A5 | 0.24 |
| Example A12 | 0.43 |
| Example B1 | 0.12 |
| Example B4 | 0.098 |
| Example B5 | 0.098 |
| Example B6 | 0.25 |
| Example C1 | 1 |
| Example C2 | 1.2 |
| Example C3 | 1.6 |
| Example C4 | 0.41 |
| Example C5 | 1.9 |
| Example C6 | 1.2 |
| Example C7 | 0.39 |

Example 1

A compound of formula (I) can be used in a manner known per se as the active ingredient for the production of tablets of the following composition:

| | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example 2

A compound of formula (I) can be used in a manner known per se as the active ingredient for the production of capsules of the following composition:

| | Per capsule |
|---|---|
| Active ingredient | 100.0 mg |
| Corn starch | 20.0 mg |

-continued

| | Per capsule |
|---|---|
| Lactose | 95.0 mg |
| Talc | 4.5 mg |
| Magnesium stearate | 0.5 mg |
| | 220.0 mg |

Example 3

A compound of formula (I) can be used in a manner known per se as the active ingredient for the production of an infusion solution of the following composition:

| | |
|---|---|
| Active ingredient | 100 mg |
| Lactic acid 90% | 100 mg |
| NaOH q.s. or HCl q.s. for adjustment to pH 4.0 | |
| Sodium chloride q.s. or glucose q.s. for adjustment of the osmolality to 290 mOsm/kg | |
| Water for injection (WFI) | ad 100 ml |

Example 4

A compound of formula (I) can be used in a manner known per se as the active ingredient for the production of an infusion solution of the following composition:

| | |
|---|---|
| Active ingredient | 100 mg |
| Hydroxypropyl-beta-cyclodextrin | 10 g |
| NaOH q.s. or HCl q.s. for adjustment to pH 7.4 | |
| Sodium chloride q.s. or glucose q.s. for adjustment of the osmolality to 290 mOsm/kg | |
| Water for injection (WFI) | ad 100 ml |

The invention claimed is:

1. A compound of formula (I):

(I)

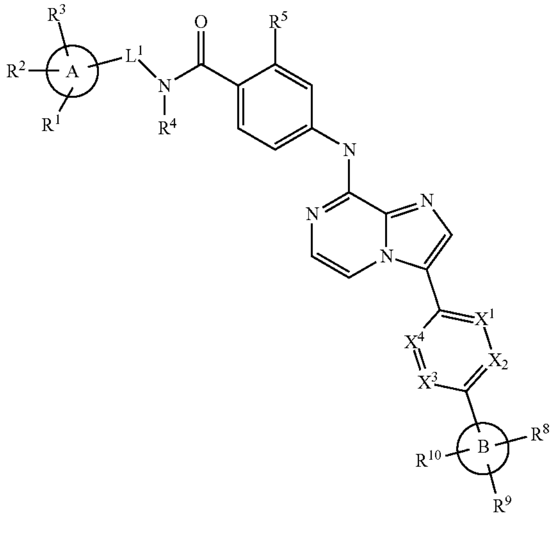

or a pharmaceutically acceptable salt thereof, wherein:

$X^1$ is N or C—$R^6$;

$X^2$ is N or C—$R^7$;

$X^3$ is N or C—$R^{11}$;

$X^4$ is N or C—$R^{12}$;

provided that at most one of $X^1$ to $X^4$ is N;

$R^1$, $R^2$, and $R^3$ are each independently selected from the group consisting of hydrogen, hydroxy, amino, halogen, cyano, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, carbamoyl-$C_1$-$C_6$-alkyl, carboxy-$C_1$-$C_6$-alkyl, $C_1$-$C_6$-alkoxy, halo-$C_1$-$C_6$-alkoxy, and a group

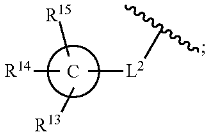

$R^4$ is hydrogen or $C_1$-$C_6$-alkyl;

$R^5$ is selected from the group consisting of hydrogen, halogen, cyano, $C_1$-$C_6$-alkyl, $C_1$-$C_6$-alkoxy, halo-$C_1$-$C_6$-alkyl, hydroxy-$C_1$-$C_6$-alkyl, and halo-$C_1$-$C_6$-alkoxy;

$R^6$, $R^7$, $R^{11}$, and $R^{12}$ are each independently selected from the group consisting of hydrogen, hydroxy, amino, halogen, cyano, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, and halo-$C_1$-$C_6$-alkoxy;

$R^8$, $R^9$, and $R^{10}$ are each independently selected from the group consisting of hydrogen, halogen, cyano, amino, hydroxy, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, halo-$C_1$-$C_6$-alkoxy, and $C_1$-$C_6$-alkoxy-$C_1$-$C_6$-alkyl;

$R^{13}$, $R^{14}$, and $R^{15}$ are each independently selected from the group consisting of hydrogen, halogen, cyano, amino, hydroxy, $C_1$-$C_6$-alkyl, halo-$C_1$-$C_6$-alkyl, cyano-$C_1$-$C_6$-alkyl, hydroxy-$C_1$-$C_6$-alkyl, amino-$C_1$-$C_6$-alkyl, $C_1$-$C_6$-alkoxy, and halo-$C_1$-$C_6$-alkoxy;

A and C are each independently a 3- to 14-membered heterocycle;

B is a 5- to 14-membered heteroaryl; and $L^1$ and $L^2$ are each independently selected from the group consisting of a covalent bond, carbonyl, and $C_1$-$C_6$-alkyldiyl.

2. The compound of claim 1, or a pharmaceutically acceptable salt thereof, wherein:

$X^1$ is C—$R^6$.

3. The compound of claim 1, or a pharmaceutically acceptable salt thereof, wherein:

$X^2$ is N or C—$R^7$.

4. The compound of claim 1, or a pharmaceutically acceptable salt thereof, wherein:

$X^3$ is C—$R^{11}$.

5. The compound of claim 1, or a pharmaceutically acceptable salt thereof, wherein:

$X^4$ is C—$R^{12}$.

6. The compound of claim 1, or a pharmaceutically acceptable salt thereof, wherein:

$R^1$ is selected from hydrogen, $C_1$-$C_6$-alkyl, hydroxy-$C_1$-$C_6$-alkyl, carbamoyl-$C_1$-$C_6$-alkyl, carboxy-$C_1$-$C_6$-alkyl, and

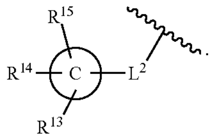

7. The compound of formula (I) according to any one of claims 1 to 6, or a pharmaceutically acceptable salt thereof, wherein:

$R^2$ is selected from the group consisting of hydrogen, $C_1$-$C_6$-alkyl, and carboxy-$C_1$-$C_6$-alkyl.

8. The compound of formula (I) according to any one of claims 1 to 6, or a pharmaceutically acceptable salt thereof, wherein:

$R^8$ is $C_1$-$C_6$-alkyl or $C_1$-$C_6$-alkoxy-$C_1$-$C_6$-alkyl.

9. The compound of claim 1, or a pharmaceutically acceptable salt thereof, wherein:

$L^1$ is $C_1$-$C_6$-alkyldiyl.

10. The compound of claim 1, or a pharmaceutically acceptable salt thereof, wherein:

$L^2$ is $C_1$-$C_6$-alkyldiyl.

11. The compound of claim 1, or a pharmaceutically acceptable salt thereof, wherein:

A is piperidyl.

12. The compound of claim 1, or a pharmaceutically acceptable salt thereof, wherein:

B is pyrazolyl.

13. The compound of claim 1, or a pharmaceutically acceptable salt thereof, wherein:

C is azetidinyl.

14. The compound of claim 1, or a pharmaceutically acceptable salt thereof, wherein:

$X^1$ is C—$R^6$;
$X^2$ is N or C—$R^7$;
$X^3$ is C—$R^{11}$;
$X^4$ is C—$R^{12}$;
$R^1$ is selected from the group consisting of hydrogen, $C_1$-$C_6$-alkyl, hydroxy-$C_1$-$C_6$-alkyl, carbamoyl-$C_1$-$C_6$-alkyl, carboxy-$C_1$-$C_6$-alkyl, and

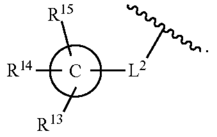

$R^2$ is selected from the group consisting of hydrogen, $C_1$-$C_6$-alkyl, and carboxy-$C_1$-$C_6$-alkyl;
$R^3$, $R^4$, $R^{13}$, $R^{14}$, and $R^{15}$ are hydrogen;
$R^5$ is $C_1$-$C_6$-alkyl;
$R^6$, $R^7$, and $R^{11}$ are each independently hydrogen or halogen;
$R^8$ is selected from the group consisting of $C_1$-$C_6$-alkyl, halo-$C_1$-$C_6$-alkyl, cyano-$C_1$-$C_6$-alkyl, and $C_1$-$C_6$-alkoxy-$C_1$-$C_6$-alkyl;
$R^9$, $R^{10}$, and $R^{12}$ are each independently hydrogen or $C_1$-$C_6$-alkyl;
A and C are each independently a 3- to 14-membered heterocycle;
B is a 5- to 14-membered heteroaryl; and
$L^1$ and $L^2$ are each independently $C_1$-$C_6$-alkyldiyl.

15. The compound of claim 1, or a pharmaceutically acceptable salt thereof, wherein:

$X^1$ is C—$R^6$;
$X^2$ is N or C—$R^7$;
$X^3$ is C—$R^{11}$;
$X^4$ is C—$R^{12}$;
$R^1$ is

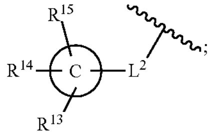

$R^2$ is $C_1$-$C_6$-alkyl or carboxy-$C_1$-$C_6$-alkyl;
$R^3$, $R^4$, $R^{11}$, $R^{12}$, $R^{13}$, $R^{14}$, and $R^{15}$ are hydrogen;
$R^5$ is $C_1$-$C_6$-alkyl;
$R^6$ and $R^7$ are halogen;
$R^8$ is $C_1$-$C_6$-alkyl or $C_1$-$C_6$-alkoxy-$C_1$-$C_6$-alkyl;
$R^9$ and $R^{10}$ are each independently hydrogen or $C_1$-$C_6$-alkyl;
A and C are each independently a 3- to 14-membered heterocycle;
B is a 5- to 14-membered heteroaryl; and
$L^1$ and $L^2$ are each independently $C_1$-$C_6$-alkyldiyl.

16. The compound of claim 1, or a pharmaceutically acceptable salt thereof, wherein:

$X^1$ is C—$R^6$;
$X^2$ is N or C—$R^7$;
$X^3$ is C—$R^{11}$;
$X^4$ is C—$R^{12}$;
$R^1$ is

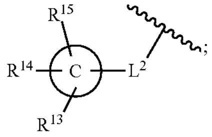

$R^2$ is methyl or carboxymethyl;
$R^3$, $R^4$, $R^{11}$, $R^{12}$, $R^{13}$, $R^{14}$, and $R^{15}$ are hydrogen;
$R^5$ is ethyl;
$R^6$ and $R^7$ are fluoro;
$R^8$ is methyl or 2-methoxyethyl;
$R^9$ and $R^{10}$ are each independently hydrogen or methyl;
A is piperidyl;
B is pyrazolyl;
C is azetidinyl; and
$L^1$ and $L^2$ are —$CH_2$—.

17. The compound of claim 1, or a pharmaceutically acceptable salt thereof, wherein the compound is selected from the group consisting of:

N-[[1-(azetidin-3-ylmethyl)-4-piperidyl]methyl]-4-[[3-[2,3-difluoro-4-(3-methyl-1H-pyrazol-4-yl)phenyl]imidazo[1,2-a]pyrazin-8-yl]amino]-2-ethyl-benzamide;
N-[[1-(azetidin-3-ylmethyl)-1-methyl-piperidin-1-ium-4-yl]methyl]-4-[3-[2,3-difluoro-4-(3-methyl-1H-pyrazol-4-yl)phenyl]imidazo[1,2-a]pyrazin-8-yl]amino]-2-ethyl-benzamide;
2-[1-(azetidin-3-ylmethyl)-4-[4-[[3-[2,3-difluoro-4-(3-methyl-1H-pyrazol-4-yl)phenyl]imidazo[1,2-a]pyrazin-8-yl]amino]-2-ethyl-benzoyl]amino]methyl]piperidin-1-ium-1-yl]acetic acid;

2-[4-[[[4-[3-[2,3-difluoro-4-(3-methyl-1H-pyrazol-4-yl) phenyl]imidazo[1,2-a]pyrazin-8-yl]amino]-2-ethyl-benzoyl]amino]methyl]-1-piperidyl]acetic acid;

2-[4-[[[4-[[3-[2,3-difluoro-4-(3-methyl-1H-pyrazol-4-yl) phenyl]imidazo[1,2-a]pyrazin-8-yl]amino]-2-ethyl-benzoyl]amino]methyl]-1-methyl-piperidin-1-ium-1-yl]acetic acid;

N-[1-(azetidin-3-ylmethyl)-4-piperidyl]methyl]-4-[3-[2,3-difluoro-4-[3-(trifluoromethyl)-1H-pyrazol-4-yl] phenyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-4-[[3-[2,3-difluoro-4-[3-(trifluoromethyl)-1H-pyrazol-4-yl]phenyl]imidazo[1,2-a]pyrazin-8-yl] amino]-2-ethyl-benzamide;

N-[[1-(2-amino-2-oxo-ethyl)-1-methyl-piperidin-1-ium-4-yl]methyl]-4-[3-[4-[1-(cyanomethyl)-3-methyl-pyrazol-4-yl]-2,3-difluoro-phenyl]imidazo[1,2-a]pyrazin-8-yl]amino]-2-ethyl-benzamide;

N-[1-(2-amino-2-oxo-ethyl)-1-methyl-piperidin-1-ium-4-yl]methyl]-4-[3-[2,3-difluoro-4-(3-methyl-1H-pyrazol-4-yl)phenyl]imidazo[1,2-a]pyrazin-8-yl]amino]-2-ethyl-benzamide;

2-[1-(2-amino-2-oxo-ethyl)-4-[[4-[3-[2,3-difluoro-4-(3-methyl-1H-pyrazol-4-yl)phenyl]imidazo[1,2-a] pyrazin-8-yl]amino]-2-ethyl-benzoyl]amino]methyl] piperidin-1-ium-1-yl]acetic acid;

2-[1-(carboxymethyl)-4-[4-[3-[2,3-difluoro-4-(3-methyl-1H-pyrazol-4-yl)phenyl]imidazo[1,2-a]pyrazin-8-yl] amino]-2-ethyl-benzoyl]amino]methyl]piperidin-1-ium-1-yl]acetic acid;

N-[[1-(azetidin-3-ylmethyl)-4-piperidyl]methyl]-2-ethyl-4-[3-[2-fluoro-6-(3-methyl-1H-pyrazol-4-yl)-3-pyridyl]imidazo[1,2-a]pyrazin-8-yl]amino]benzamide;

N-[[1-(azetidin-3-ylmethyl)-1-methyl-piperidin-1-ium-4-yl]methyl]-2-ethyl-4-[[3-[2-fluoro-6-(3-methyl-1H-pyrazol-4-yl)-3-pyridyl]imidazo[1,2-a]pyrazin-8-yl] amino]benzamide;

N-[1-(azetidin-3-ylmethyl)-4-piperidyl]methyl]-4-[[3-[6-(3,5-dimethyl-1H-pyrazol-4-yl)-2-fluoro-3-pyridyl] imidazo[1,2-a]pyrazin-8-yl]amino]-2-ethyl-benzamide;

N-[1-(azetidin-3-ylmethyl)-1-methyl-piperidin-1-ium-4-yl]methyl]-4-[3-[6-(3,5-dimethyl-1H-pyrazol-4-yl)-2-fluoro-3-pyridyl]imidazo[1,2-a]pyrazin-8-yl]amino]-2-ethyl-benzamide;

N-[[1-(azetidin-3-ylmethyl)-1-methyl-piperidin-1-ium-4-yl]methyl]-2-ethyl-4-[[3-[5-fluoro-6-(3-methyl-1H-pyrazol-4-yl)-3-pyridyl]imidazo[1,2-a]pyrazin-8-yl] amino]benzamide;

N-[[1-(azetidin-3-ylmethyl)-1-methyl-piperidin-1-ium-4-yl]methyl]-2-ethyl-4-[[3-[4-methyl-6-(3-methyl-1H-pyrazol-4-yl)-3-pyridyl]imidazo[1,2-a]pyrazin-8-yl] amino]benzamide;

N-[[1-(azetidin-3-ylmethyl)-1-methyl-piperidin-1-ium-4-yl]methyl]-2-ethyl-4-[[3-[4-(3-methyl-1H-pyrazol-4-yl)phenyl]imidazo[1,2-a]pyrazin-8-yl]amino]benzamide;

4-[3-[2,3-difluoro-4-(3-methyl-1H-pyrazol-4-yl)phenyl] imidazo[1,2-a]pyrazin-8-yl]amino]-2-ethyl-N-(4-piperidylmethyl) benzamide;

N-[[1-(azetidin-3-ylmethyl)-1-methyl-piperidin-1-ium-4-yl]methyl]-4-[3-[2,3-difluoro-4-[1-(2-methoxyethyl)-3,5-dimethyl-pyrazol-4-yl]phenyl]imidazo[1,2-a] pyrazin-8-yl]amino]-2-ethyl-benzamide;

N-[1-(2-amino-2-oxo-ethyl)-1-methyl-piperidin-1-ium-4-yl]methyl]-4-[3-[2,3-difluoro-4-[1-(2-methoxyethyl)-3,5-dimethyl-pyrazol-4-yl]phenyl]imidazo[1,2-a] pyrazin-8-yl]amino]-2-ethyl-benzamide;

4-[3-[2,3-difluoro-4-[1-(2-methoxyethyl)-3,5-dimethyl-pyrazol-4-yl]phenyl]imidazo[1,2-a]pyrazin-8-yl] amino]-2-ethyl-N-[1-(2-hydroxyethyl)-1-methyl-piperidin-1-ium-4-yl]methyl]benzamide;

4-[[3-[2,3-difluoro-4-[1-(2-methoxyethyl)-3-methyl-pyrazol-4-yl]phenyl]imidazo[1,2-a]pyrazin-8-yl] amino]-N-[(1,1-dimethylpiperidin-1-ium-4-yl) methyl]-2-ethyl-benzamide;

N-[[1-(2-amino-2-oxo-ethyl)-1-methyl-piperidin-1-ium-4-yl]methyl]-4-[[3-[2,3-difluoro-4-[1-(2-methoxy-ethyl)-3-methyl-pyrazol-4-yl]phenyl]imidazo[1,2-a] pyrazin-8-yl]amino]-2-ethyl-benzamide;

4-[[3-[2,3-difluoro-4-[1-(2-methoxyethyl)-3-methyl-pyrazol-4-yl]phenyl]imidazo[1,2-a]pyrazin-8-yl] amino]-2-ethyl-N-[[1-(2-hydroxyethyl)-1-methyl-piperidin-1-ium-4-yl]methyl]benzamide; and N-[1-(azetidin-3-ylmethyl)-1-methyl-piperidin-1-ium-4-yl]methyl]-4-[3-[2,3-difluoro-4-[1-(2-methoxyethyl)-3-methyl-pyrazol-4-yl]phenyl]imidazo[1,2-a]pyrazin-8-yl]amino]-2-ethyl-benzamide.

18. A pharmaceutical composition comprising a compound of claim 1, or a pharmaceutically acceptable salt thereof, and a therapeutically inert carrier.

19. A process of manufacturing the compounds of formula (I) according to claim 1, or pharmaceutically acceptable salts thereof, the process comprising:

(i) Suzuki coupling of a heteroaryl halide C1, wherein $R^1$ to $R^5$, A, and $L^1$ are as defined herein and "Hal" is a halogen, preferably iodine, (C1)

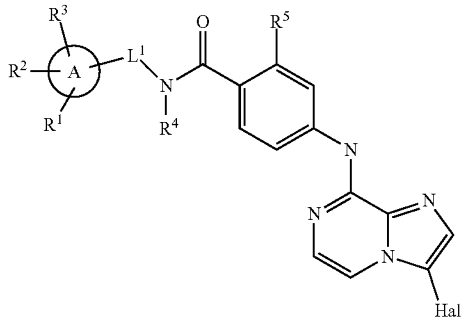

with a boronic acid (ester) B1, wherein $X^1$ to $X^4$, $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(B1)

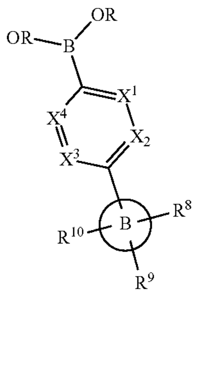

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I); or (ii) Suzuki coupling of an aryl/heteroaryl halide E1, wherein $R^1$ to $R^5$, A, $L^1$, and $X^1$ to $X^4$ are as defined herein and "Hal" is a halogen, preferably chlorine, (E1)

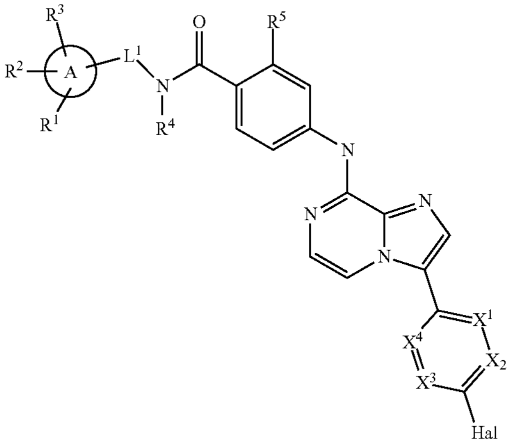

with a boronic acid (ester) I1, wherein $R^8$ to $R^{10}$ and ring B are as defined herein, and each R is independently hydrogen or alkyl, wherein the two R groups, taken together with the oxygen and boron atoms to which they are attached, may form a cyclic boronic acid ester;

(I1)

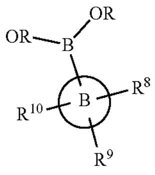

in the presence of a transition metal catalyst, such as 1,1'-bis(diphenylphosphino)ferrocene-palladium(II) dichloride dichloromethane complex or Tris(dibenzylideneacetone)dipalladium(0), to afford said compound of formula (I).

20. A method for the treatment or prevention of infections and resulting diseases caused by *Enterococcus faecium, Staphylococcus aureus, Klebsiella pneumoniae, Acinetobacter baumannii, Pseudomonas aeruginosa, Enterobacter* species or *E. coli*, or a combination thereof, the method comprising administering a compound of claim 1, or a pharmaceutically acceptable salt thereof, to a mammal in need thereof.

* * * * *